United States Patent [19]

Krämer et al.

[11] Patent Number: 4,668,700

[45] Date of Patent: May 26, 1987

[54] PEST-COMBATING AGENTS

[75] Inventors: Wolfgang Krämer; Wolf Reiser; Dieter Berg, all of Wuppertal; Wilhelm Brandes, Paul Reinecke, both of Leverkusen, all of Fed. Rep. of Germany

[73] Assignee: Bayer Aktiengesellschaft, Leverkusen, Fed. Rep. of Germany

[21] Appl. No.: 630,624

[22] Filed: Jul. 13, 1984

Related U.S. Application Data

[62] Division of Ser. No. 496,776, May 20, 1983, Pat. No. 4,503,059.

[30] Foreign Application Priority Data

Jun. 4, 1982 [DE] Fed. Rep. of Germany ....... 3221138
Feb. 19, 1983 [DE] Fed. Rep. of Germany ....... 3305769

[51] Int. Cl.$^4$ .................... C07D 317/28; A01N 43/28
[52] U.S. Cl. ..................................... 514/467; 514/184; 549/451; 549/373; 548/262; 548/336; 71/88
[58] Field of Search ............... 549/373, 451; 514/467, 514/184; 548/262; 71/88

[56]  References Cited

U.S. PATENT DOCUMENTS

| 2,445,393 | 7/1948 | Fourneau | 549/451 |
| 3,337,408 | 8/1967 | McClure | 514/467 |
| 4,141,908 | 2/1979 | Heeres | 549/451 |
| 4,526,994 | 7/1985 | Niedballa et al. | 549/451 |
| 4,607,045 | 8/1986 | Janseen et al. | 549/451 |

FOREIGN PATENT DOCUMENTS

| 2200766 | 7/1972 | Fed. Rep. of Germany | 514/467 |
| 2163322 | 7/1973 | France | 514/467 |
| 7200826 | 8/1972 | Netherlands | 514/467 |
| 0601612 | 5/1948 | United Kingdom | 514/467 |

OTHER PUBLICATIONS

Chem. Reviews, vol. 47 (Dec. 1950).
Triggle et al.; CA 57:12450c-i, 12451-z (1962), Studies on Chemical Basis for Cholinomimetic Activity.
Brimblecombe et al.; CA 74:62865x (1971), Structure Activity Relations for 1,3-Dioxalanes.
Sokolov et al.; CA 78:147848b (1973), Synthesis and Curarelike Prop. of Quaternary Ammonium Derivatives.
Wolinski et al.; CA 94:15615u (1981) Search for Anticholinergic Compounds XVII.

*Primary Examiner*—Glennon H. Hollrah
*Assistant Examiner*—D. L. Dinner
*Attorney, Agent, or Firm*—Sprung Horn Kramer & Woods

[57]  ABSTRACT

Substituted aminoketals of the formula

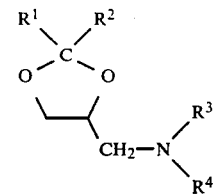

in which
$R^1$ to $R^4$ are various organic radicals and
$R^2$ may also be hydrogen, are fungicidally active. Some of the compounds are new.

13 Claims, No Drawings

PEST-COMBATING AGENTS

This is a division of application Ser. No. 496,776, filed May 20, 1983 now U.S. Pat. No. 4,503,059.

The present invention relates to the use of substituted aminoketals, some of which are known, as pest-combating agents.

It has already been disclosed that certain aminoketals, such as, for example, 2-methyl-2-(3,4,5-trimethoxyphenyl)-4-(pyrrolidin-1-ylmethyl)-1,3-dioxolane, 2-cyclohexyl-2-phenyl-4-(morpholin-1-ylmethyl)-1,3-dioxolane, 2-phenyl-2-chloromethyl-4-(morpholin-1-ylmethyl)-1,3-dioxolane and 2-methyl-2-(4-methyl-but-3-en-1-yl)-4-(piperidin-1-ylmethyl)-1,3-dioxolane, exhibit an action, for example as diuretics or hypotensive agents, in the pharmaceuticals sector [see, for example, French Patent Specification No. 2,163,322; Japanese Patent Application No. 52-33,608; Belgian Patent Specification No. 776,421; Dutch Patent Specification No. 6,609,579; U.S. Pat. No. 3,337,408 and U.S.S.R. Patent Specification No. 722,910; and also A. R. Patel et al., "J. Pharm. Sci. 52 (1963), No. 6, pages 588–592; J. Wolinski et al., "Acta Pol. Pharm. 1980, 37 (1), pages 15–24 (Polish), 1978, 35 (6), pages 621–627 (Polish), 1978, 35 (3), pages 265–272 (Polish) and 1977, 34 (2), pages 143–147 (Polish)].

Furthermore, aminoketals, such as, for example, 2,2-dimethyl-4-(morpholin-1-ylmethyl)-1,3-dioxolane, are known as intermediate products or starting materials for the preparation of other pharmaceutically active compounds [see, for example, N. D. Harris, "J. Org. Chem. 28 (1963), No. 3, pages 745–748 and Karpysow "Bio-Org. Khim" 1979, 5, (2), pages 238–241 (Russian)]. None of the known aminoketals are known to have an action in the field of plant protection.

Furthermore, it has already been disclosed that aminopropiophenone derivatives, such as, for example, 4-tert.-butylphenyl 1-dimethylamino-prop-2-yl ketone (see DE-OS [German Published Specification] No. 3,019,497), as well as organic sulphur compounds, such as, for example, zinc ethylene-1,2-bis-(dithiocarbamate) (see R. Wegler, "Chemie der Pflanzenschutz- und Schädlingsbekämpfungsmittel" [Chemistry of Plant Protection Agents and Pest-combating Agents], Springer Verlag Berlin 1970, Volume 2, page 65 et seq.), possess fungicidal properties. However, the action of these compounds is not always completely satisfactory in some fields of use, in particular when low amounts and concentrations are used.

It has been found that substituted aminoketals, some of which are known, of the formula (I)

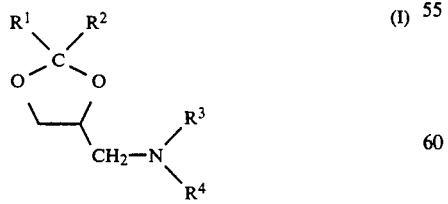

in which
R$^1$ represents optionally substituted alkyl, or represents alkenyl and alkinyl, or optionally substituted cycloalkyl, optionally substituted aralkenyl or optionally substituted aryl,
R$^2$ has the same meaning as R$^1$ and furthermore represents hydrogen,
R$^3$ represents alkyl, alkenyl, alkinyl, optionally substituted cycloalkyl, optionally substituted aryl or optionally substituted aralkyl,
R$^4$ represents alkyl, alkenyl, alkinyl, optionally substituted cycloalkyl, optionally substituted aryl or optionally substituted aralkyl, or R$^3$ and R$^4$, together with the nitrogen atom to which they are bonded, represent an optionally substituted heterocyclic structure which can contain further heteroatoms, and their physiologically tolerated acid addition salts and metal salt complexes, have fungicidal properties.

The compounds of the formula (I) can occur as geometric isomers or isomer mixtures of different compositions. The pure isomers as well as the isomer mixtures are claimed according to the invention.

Surprisingly, the substituted aminoketals of the formula (I) to be used in accordance with the invention exhibit a more pronounced fungicidal action than the compounds known from the prior art, namely 4-tert.-butylphenyl 1-dimethylaminoprop-2-yl ketone and zinc ethylene-1,2-bis-(dithiocarbamate), which are compounds having the same direction of action. The substances according to the invention thus represent an enrichment of the art.

Formula (I) gives a general definition of the substituted aminoketals to be used in accordance with the invention. Preferred compounds are those in which
R$^1$ represents straight-chain or branched alkyl having 1 to 18 carbon atoms; substituted alkyl, such as straight-chain or branched halogenoalkyl having 1 to 12 carbon atoms and 1 to 5 halogen atoms, straight-chain or branched cyanoalkyl having 1 to 4 carbon atoms in the alkyl part, aralkyl, aryloxyalkyl, aralkyloxyalkyl, arylthioalkyl, arylsulphinylalkyl and arylsulphonylalkyl, each having 1 to 6 carbon atoms in each alkyl part and 6 to 10 carbon atoms in the aryl part, the radicals in each case being optionally monosubstituted or polysubstituted by identical or different substituents, the following being suitable aryl substituents in each case: halogen, cyano, nitro; alkyl, alkoxy and alkylthio, each having 1 to 4 carbon atoms; halogenoalkyl, halogenoalkoxy, halogenoalkylthio, each having 1 or 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, in particular fluorine or chlorine, or by alkyl having 1 to 4 carbon atoms; and represents cycloalkylalkyl having 1 to 4 carbon atoms in the alkyl part and 3 to 7 carbon atoms in the cycloalkyl part which is optionally monosubstituted or polysubstituted by alkyl having 1 to 4 carbon atoms, and also represents straight-chain or branched alkenyl or alkinyl, each having 2 to 6 carbon atoms, cycloalkyl which has 3 to 7 carbon aoms and is optionally monosubstituted or polysubstituted by identical or different alkyl radicals having 1 to 4 carbon atoms, or represents aryl having 6 to 10 carbon atoms and arylalkenyl having 2 to 6 carbon atoms in the alkenyl part and 6 to 10 carbon atoms in the aryl part, each of which is optionally monosubstituted or polysubstituted by identical or different substituents, suitable aryl substituents in each case being: halogen, cyano, nitro; alkyl, alkoxy, alkylthio, each having 1 to 4 carbon atoms; halogenoalkyl, halogenoalkoxy, halogenoalkylthio, each having 1 to 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, in particular fluorine or chlorine, or by alkyl having 1 to 4 carbon atoms;

$R^2$ has the same meaning as $R^1$ and may be identical or different to this radical, and additionally represents hydrogen, $R^3$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloalkyl which has 5 to 7 carbon atoms and is optionally monosubstituted or polysubstituted by identical or different alkyl groups having 1 to 4 carbon atoms, and aryl having 6 to 10 carbon atoms or aralkyl having 1 or 2 carbon atoms in the aryl part, each of which radicals is optionally monosubstituted or polysubstituted by identical or different substituents, suitable aryl substituents in each case being: halogen, alkyl having 1 to 4 carbon atoms and halogenoalkyl having 1 or 2 carbon atoms and 1 to 5 halogen atoms;

$R^4$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloalkyl which has 5 to 7 carbon atoms and is optionally monosubstituted or polysubstituted by identical or different alkyl groups having 1 to 4 carbon atoms, and aryl having 6 to 10 carbon atoms or aralkyl having 1 to 2 carbon atoms in the alkyl part and 6 to 10 carbon atoms in the aryl part, each of which radicals is optionally monosubstituted or polysubstituted by identical or different substituents, suitable aryl substituents in each case being; halogen, alkyl having 1 to 4 carbon atoms and halogenoalkyl having 1 or 2 carbon atoms and 1 to 5 halogen atoms; or $R^3$ and $R^4$, together with the nitrogen atom to which they are bonded, represent a 5-membered to 7-membered, saturated or unsaturated heterocyclic structure, which has 1 to 3 heteroatoms, preferably nitrogen or oxygen, and is optionally monosubstituted or polysubstituted by identical or different substituents, the following being preferably mentioned as substituents: alkyl having 1 to 4 carbon atoms, alkoxycarbonyl having 1 to 4 carbon atoms in the alkyl part and phenyl.

Particularly preferred substituted aminoketals of the formula (I) are those in which $R^1$ represents straight-chain or branched alkyl having 1 to 12 carbon atoms, cyclopropyl, cyclopentyl, cyclohexyl, straight-chain or branched halogenoalkyl having 1 to 6 carbon atoms and 1 to 5 halogen atoms, or phenyl, phenylalkyl, phenoxyalkyl, benzyloxyalkyl, phenylthioalkyl, phenylsulphinylalkyl and phenylsulphonylalkyl, each having 1 to 5 carbon atoms in the alkyl part, the radicals in each case being optionally monosubstituted, disubstituted or trisubstituted by identical or different substituents, and phenylalkenyl which has 2 to 4 carbon atoms in the alkenyl part and is optionally monosubstituted, disubstituted or trisubstituted by identical or different substituents, particularly preferred phenyl substituents being: fluorine, chlorine, bromine, cyano, nitro, methyl, methoxy, methylthio, ethyl, ethoxy, ethylthio, n- and i-propyl, isopropoxy, n-, iso-, sec.- and t-butyl, trifluoromethyl, trifluoromethoxy, trifluoromethylthio, cyclohexyl, methoxycarbonyl, ethoxycarbonyl and phenoxy or phenyl which is optionally substituted by fluorine, chlorine or methyl;

$R^2$ represents straight-chain or branched alkyl having 1 to 10 carbon atoms, benzyl and phenyl which is optionally monosubstituted, disubstituted or trisubstituted by identical or different substituents, suitable phenyl or benzyl substituents in each case being: fluorine, chlorine, bromine, cyano, nitro, trifluoromethyl, trifluoromethoxy, trifluoromethylthio, methoxycarbonyl and ethoxycarbonyl, or represents cyclopropyl, cyclopentyl and cyclohexyl, $R^3$ represents methyl, ethyl, n- and i-propyl, n-, i-, sec.- and t-butyl, n-pentyl, n-hexyl, n-heptyl, n-octyl, n-nonyl, n-decyl, n-dodecyl, allyl, propargyl, 2-butenyl, cyclopentyl or cyclohexyl, and phenyl or benzyl, each of which is optionally monosubstituted or disubstituted by identical or different substituents from the group comprising fluorine, chlorine, methyl and trifluoromethyl, and $R^4$ represents n- and i-propyl, n-, i-, sec.- and t-butyl, n-pentyl, n-hexyl, n-heptyl, n-octyl, n-nonyl, n-decyl, allyl, propargyl, but-2-enyl, cyclopentyl or cyclohexyl, and phenyl or benzyl, each of which is optionally monosubstituted or disubstituted by identical or different substituents from the group comprising fluorine, chlorine, methyl and trifluoromethyl; or $R^3$ and $R^4$, together with the nitrogen atom to which they are bonded, represent pyrrolidin-1-yl, piperidin-1-yl, piperazin-1-yl, morpholin-4-yl, perhydroazepin-1-yl, imidazol-1-yl, 1,2,4-triazol-1-yl or pyrazol-1-yl, each of which is optionally monosubstituted, disubstituted or trisubstituted by identical or different substituents, particularly preferred substituents being: methyl, ethyl, n- and i-propyl, phenyl, methoxycarbonyl and ethoxycarbonyl.

Very particularly preferred substituted aminoketals of the formula (I) are those in which $R^1$ represents straight-chain or branched alkyl having 1 to 5 carbon atoms, and phenylalkenyl, phenylalkyl, phenoxyalkyl, benzyloxyalkyl, phenylthioalkyl, phenylsulphinylalkyl and phenylsulphonylalkyl, each of which has up to 5 carbon atoms in the alkyl part or alkenyl part and is optionally monosubstituted, disubstituted or trisubstituted by identical or different substituents, the following being mentioned as phenyl substituents: fluorine, chlorine, bromine, methyl, ethyl, n- and i-propyl, t-butyl-, methoxy, ethoxy, isopropoxy, cyclohexyl, trifluoromethyl, trifluoromethoxy, trifluoromethylthio, methoxycarbonyl, ethoxycarbonyl, nitro, cyano, phenyl and phenoxy;

$R^2$ represents straight-chain or branched alkyl having 1 to 4 carbon atoms or hydrogen;

$R^3$ represents methyl, ethyl, n- and i-propyl or n-, i- and t-butyl;

$R^4$ represents methyl, ethyl, n- and i-propyl, n- and i-butyl, pentyl or hexyl, or $R^3$ and $R^4$, together with the nitrogen atom to which they are bonded, represent piperidin-1-yl, perhydroazepin-1-yl, pyrrolidin-1-yl, morpholin-4-yl, piperazin-1-yl, imidazol-1-yl and 1,2,4-triazol-1-yl, each of which is optionally monosubstituted, disubstituted or trisubstituted by identical or different substituents, the following being mentioned as substituents: alkyl having 1 to 3 carbon atoms, methoxycarbonyl, ethoxycarbonyl and phenyl.

Substituted aminoketals of the formula (I) which may be mentioned in particular are those in which
 $R^1$ represents the groupings

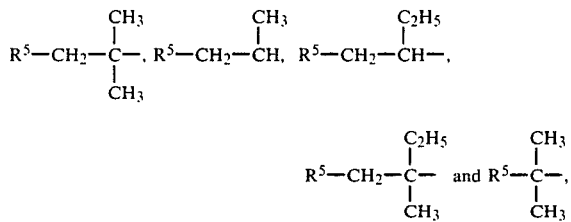

$R^5$ represents phenyl, phenoxy, phenylthio, phenylsulphinyl or phenylsulphonyl, each of which is optionally monosubstituted to trisubstituted by identical or different substituents, the following being mentioned as substituents: fluorine, chlorine, bromine, nitro, cyclohexyl, straight-chain or branched alkyl having 1 to 4 carbon atoms, straight-chain or branched alkoxy having 1 to 3 carbon atoms and alkoxycarbonyl having 1 or 2 carbon atoms in the alkoxy part, $R^2$ represents a straight-chain or branched alkyl having 1 to 4 carbon atoms, $R^3$ represents a straight-chain or branched alkyl having 1 to 4 carbon atoms or straight-chain or branched alkenyl having 3 to 5 carbon atoms, $R^4$ represents straight-chain or branched alkyl having 1 to 4 carbon atoms, and $R^3$ and $R^4$, together with the nitrogen atom to which they are bonded, represent a piperidine, morpholine or pyrrolidine radical which is optionally monosubstituted to trisubstituted by identical or different alkyl radicals having 1 to 3 carbon atoms, as well as those aminoketals of the formula (I) in which
 $R^1$ represents the groupings

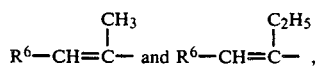

wherein
 $R^6$ represents phenyl which is in each case optionally monosubstituted to trisubstituted by identical or different substituents, the following being mentioned as substituents: fluorine, chlorine, bromine, nitro, cyclohexyl, straight-chain or branched alkyl or alkoxy, each having 1 to 4 carbon atoms, an alkoxycarbonyl having 1 or 2 carbon atoms in the alkoxy part, $R^2$ represents straight-chain or branched alkyl having 1 to 4 carbon atoms, $R^3$ represents straight-chain or branched alkyl having 1 to 4 carbon atoms or straight-chain or branched alkenyl having 3 to 5 carbon atoms, $R^4$ represents straight-chain or branched alkyl having 1 to 4 carbon atoms, and $R^3$ and $R^4$, together with the nitrogen atom to which they are bonded, represent a piperidine, morpholine or pyrrolidine radical which is optionally monosubstituted to trisubstituted by identical or different alkyl radicals having 1 to 3 carbon atoms.

The addition products of acids and the substituted aminoketals of the formula (I) and metal salt complexes of compounds of the formula (I) are also compounds which can be used according to the invention.

To prepare physiologically tolerated acid addition salts of the compounds of the formula (I), the following acids are preferred: hydrohalic acids, such as, for example, hydrochloric acid and hydrobromic acid, in particular hydrochloric acid, and also phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid and naphthalene-1,5-disulphonic acid.

The acid addition salts of the compounds of the formula (I) can be obtained in a simple manner by customary salt formation methods, for example by dissolving a compound of the formula (I) in a suitable organic solvent and adding the acid, for example hydrochloric acid, and can be isolated in a known manner, for example by filtration, and if appropriate purified by washing with an inert organic solvent.

Preferred salts for the preparation of metal salt complexes of the compounds of the formula (I) are those of metals of main groups II to IV and of subgroups I and II and IV to VIII, and copper, zinc, manganese, magnesium, tin, iron and nickel may be mentioned as examples.

Some of the substituted aminoketals of the formula (I) which are to be used according to the invention are known. The known compounds, as well as the new substituted aminoketals of the formula (IA)

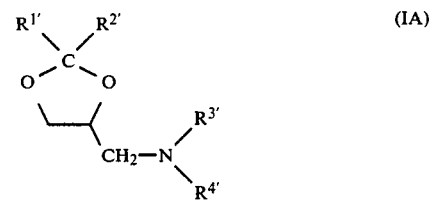

in which
 $R^{1'}$, $R^{2'}$, $R^{3'}$ and $R^{4'}$ have the meaning given further below, can be prepared by processes which are known from the literature, by reacting substituted dioxolanes of the general formula (II)

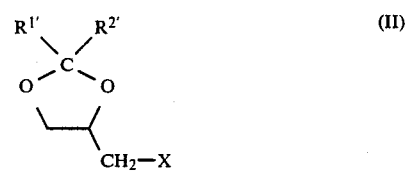

in which
 $R^{1'}$ and $R^{2'}$ have the meaning given further below and X represents halogen, optionally substituted alkylsulphonyloxy or arylsulphonyloxy,
with amines of the general formula (III)

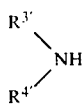

(III)

in which

R$^{3'}$ and R$^{4'}$ have the meaning given further below, if appropriate in the presence of a catalyst and, if appropriate, in the presence of a base and, if appropriate in the presence of a diluent.

In the formula (IA), the substituents have the following meaning:

R$^{1'}$ represents a straight-chain or branched alkyl having 6 to 18 carbon atoms; substituted alkyl, such as straight-chain or branched halogenoalkyl having 2 to 12 carbon atoms and 1 to 5 halogen atoms, straight-chain or branched cyanoalkyl having 1 to 4 carbon atoms in the alkyl part, benzyl which is monosubstituted or polysubstituted by identical or different substituents, arylalkyl which has 2 to 6 carbon atoms in the alkyl part and 6 to 10 carbon atoms in the aryl part and is optionally monosubstituted or polysubstituted by identical or different substituents, and aryloxyalkyl, aralkyloxyalkyl, arylthioalkyl, arylsulphinylalkyl and arylsulphonylalkyl, each of which has 1 to 6 carbon atoms in each alkyl part and 6 to 10 carbon atoms in the aryl part, suitable aryl or benzyl substituents in each case being: halogen, cyano, nitro; alkyl, alkoxy and alkylthio, each having 1 to 4 carbon atoms; halogenoalkyl, halogenoalkoxy and halogenoalkylthio, each having 1 or 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, in particular fluorine or chlorine, or by alkyl having 1 to 4 carbon atoms; cycloalkylalkyl having 1 to 4 carbon atoms and 3 to 7 atoms in the cycloalkyl part which is optionally monosubstituted or polysubstituted by alkyl having 1 to 4 carbon atoms; and also represents straight-chain or branched alkenyl having 2 to 5 carbon atoms, straight-chain or branched alkinyl having 2 to 6 carbon atoms; cycloalkyl which has 3 to 7 carbon atoms and is monosubstituted or polysubstituted by identical or different alkyl radicals having 1 to 4 carbon atoms, and represents arylalkenyl having 2 to 6 carbon atoms in the alkenyl part and 6 to 10 atoms in the aryl part, suitable aryl substituents in each case being: halogen, cyano, nitro; alkyl, alkoxy and alkylthio, each having 1 or 2 carbon atoms and 1 to 5 halogen atoms, cycloalkyl having 5 to 7 carbon atoms, alkoxycarbonyl having 1 to 4 carbon atoms in the alkyl part, phenyl or phenoxy which is optionally substituted by halogen, in particular fluorine or chlorine, or by alkyl having 1 to 4 carbon atoms;

R$^{2'}$ represents hydrogen, straight-chain or branched alkyl having 1 to 18 carbon atoms; substituted alkyl, such as straight-chain or branched halogenoalkyl having 1 to 12 carbon atoms and 1 to 5 halogen atoms, straight-chain or branched cyanoalkyl having 1 to 4 carbon atoms in the alkyl part, arylalkyl, aryloxyalkyl, aralkyloxyalkyl, arylthioalkyl, arylsulphinylalkyl and arylsulphonylalkyl, each of which has 1 to 6 carbon atoms in each alkyl part and 6 to 10 carbon atoms in the aryl part and is optionally monosubstituted or polysubstituted by identical or different substituents, suitable aryl substituents in each case being: halogen, cyano, nitro; alkyl, alkoxy and alkylthio, each having 1 to 4 carbon atoms; halogenoalkyl, halogenoalkoxy and halogenoalkylthio, each having 1 or 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, in particular fluorine or chlorine, or by alkyl having 1 to 4 carbon atoms; and cycloalkyl having 1 to 4 carbon atoms in the alkyl part and 3 to 7 carbon atoms in the cycloalkyl part which is optionally monosubstituted or polysubstituted by alkyl having 1 to 4 carbon atoms, and also represents straight-chain or branched alkenyl or alkinyl, each having 2 to 6 carbon atoms, cycloalkyl which has 3 to 7 carbon atoms and is optionally monosubstituted or polysubstituted by identical or different alkyl radicals having 1 to 4 carbon atoms, or represents aryl having 6 to 10 carbon atoms and arylalkenyl having 2 to 6 carbon atoms in the alkenyl part and 6 to 10 carbon atoms in the acyl part, each of which is optionally monosubstituted or polysubstituted by identical or different substituents, suitable aryl substituents being: halogen, cyano, nitro; alkyl, alkoxy and alkylthio, each having 1 to 4 carbon atoms; halogenoalkyl, halogenoalkoxy and halogenoalkylthio, each having 1 to 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, in particular fluorine or chlorine, or by alkyl having 1 to 4 carbon atoms;

R$^{3'}$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloalkyl which has 5 to 7 carbon atoms and is optionally monosubstituted or polysubstituted by identical or different alkyl radicals having 1 to 4 carbon atoms, and represents aryl having 6 to 10 carbon atoms and aralkyl having 1 or 2 carbon atoms in the alkyl part and 6 to 10 carbon atoms in the aryl part, each of which is optionally monosubstituted or polysubstituted by identical or different substituents, suitable aryl substituents in each case being: halogen, alkyl having 1 to 4 carbon atoms and halogenoalkyl having 1 or 2 carbon atoms and 1 to 5 halogen atoms;

R$^{4'}$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloalkyl which has 5 to 7 carbon atoms and is optionally monosubstituted or polysubstituted by identical or different alkyl radicals having 1 to 4 carbon atoms, and aryl having 6 to 10 carbon atoms or aralkyl having 1 to 2 carbon atoms in the alkyl part and 6 to 10 carbon atoms in the aryl part, each of which is optionally monosubstituted or polysubstituted by identical or different substituents, suitable aryl substituents in each case being: halogen, alkyl having 1 to 4 carbon atoms, and halogenoalkyl having 1 or 2 carbon atoms and 1 to 5 halogen atoms; or $R^{3'}$ and $R^{4'}$, together with the nitrogen atom to which they are bonded, represent a 5-membered to 7-membered, saturated or unsaturated heterocyclic structure which has 1 to 3 hetero atoms, preferably nitrogen or oxygen, and is optionally monosubstituted or polysubstituted by identical or different substituents, the following being preferably mentioned as substituents: alkyl having 1 to 4 carbon atoms, alkoxycarbonyl having 1 to 4 carbon atoms in the alkyl part, and phenyl.

Particularly preferred substituted aminoketals of the formula (IV) are those in which $R^{1'}$ represents straight-chain or branched alkyl having 6 to 12 carbon atoms; straight-chain or branched halogenoalkyl having 2 to 6 carbon atoms and 1 to 5 halogen atoms, cyanomethyl or cyanoethyl, benzyl which is monosubstituted to trisubstituted by identical or different substituents, phenylalkyl which has 2 to 6 carbon atoms in the alkyl part and is optionally monosubstituted to trisubstituted by identical or different substituents, and phenoxyalkyl, phenylalkoxyalkyl, phenylthioalkyl, phenylsulphinylalkyl and phenylsulphonylalkyl, each of which has 1 to 4 carbon atoms in each alkyl part, suitable phenyl or benzyl substituents in each case being: fluorine, chlorine, bromine, cyano, nitro, methyl, methoxy, methylthio, ethyl, ethoxy, ethylthio, n- and i-propyl, isopropoxy, n-, iso-, sec.- and t-butyl, trifluoromethyl, trifluoromethoxy, trifluoromethylthio, cyclohexyl, methoxycarbonyl and ethoxycarbonyl, and phenoxy or phenyl which is optionally substituted by fluorine, chlorine or methyl; and also represents cycloalkylalkyl having 1 to 4 carbon atoms in the alkyl part and 5 to 7 carbon atoms in the cycloalkyl part which is optionally monosubstituted or polysubstituted by alkyl having 1 to 4 carbon atoms; and also represents straight-chain or branched alkenyl having 3 to 5 carbon atoms, straight-chain or branched alkinyl having 3 to 6 carbon atoms; cycloalkyl which has 5 to 7 carbon atoms and is monosubstituted to trisubstituted by identical or different substituents from amongst methyl, ethyl or propyl, and represents phenylalkenyl having 2 to 5 carbon atoms in the alkenyl part, suitable phenyl substituents in each case being: fluorine, chlorine, bromine, cyano, nitro, methyl, methoxy, methylthio, ethyl, ethoxy, ethylthio, n- and i-propyl, isopropoxy, n-, iso-, sec.- and t-butyl, trifluoromethyl, trifluoromethoxy, trifluoromethylthio, cyclohexyl, methoxycarbonyl and ethoxycarbonyl, and phenoxy or phenyl which is optionally substituted by fluorine, chlorine or methyl;

$R^{2'}$ represents hydrogen, straight-chain or branched alkyl having 1 to 10 carbon atoms; and benzyl or phenyl which is optionally monosubstituted to trisubstituted by identical or different substituents, suitable phenyl or benzyl substituents in each case being: fluorine, chlorine, bromine, cyano, nitro, trifluoromethyl, trifluoromethoxy, trifluoromethylthio, methoxycarbonyl and ethoxycarbonyl, $R^{3'}$ represents methyl, ethyl, n- and i-propyl, n-, i-, sec.- and t-butyl, n-pentyl, n-hexyl, n-heptyl, n-octyl, n-nonyl, n-decyl, n-dodecyl, allyl, propargyl, but-2-enyl, cyclopentyl and cyclohexyl, and benzyl or phenyl, each of which is optionally monosubstituted or disubstituted by identical or different substituents from amongst fluorine, chlorine, methyl or trifluoromethyl, and $R^{4'}$ represents n- and i-propyl, n-, i-, sec.- and t-butyl, n-pentyl, n-hexyl, n-heptyl, n-octyl, n-nonyl, n-decyl, allyl, propargyl, but-2-enyl, cyclopentyl and cyclohexyl, and phenyl or benzyl, each of which is optionally monosubstituted or disubstituted by identical or different substituents from amongst fluorine, chlorine, methyl and trifluoromethyl; or $R^{3'}$ and $R^{4'}$, together with the nitrogen atom to which they are bonded, represent pyrrolidin-1-yl, piperidin-1-yl, piperazin-1-yl, morpholin-4-yl, perhydroazepin-1-yl, imidazol-1-yl, 1,2,4-triazol-1-yl or pyrazol-1-yl, each of which is optionally monosubstituted to trisubstituted by identical or different substituents, particularly preferred substituents being: methyl, ethyl, n- and i-propyl, phenyl, methoxycarbonyl and ethoxycarbonyl.

Substituted aminoketals of the formula (IA) which may be mentioned in particular are those in which $R^{1'}$ represents the groupings

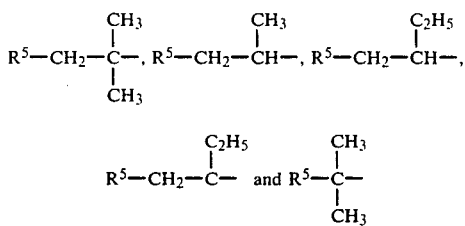

wherein $R^5$ represents phenyl, phenoxy, phenylthio, phenylsulphinyl or phenylsulphonyl, each of which is optionally monosubstituted to trisubstituted by identical or different substituents, the following being mentioned as substituents: fluorine, chlorine, bromine, nitro, cyclohexyl, straight-chain or branched alkyl having 1 to 4 carbon atoms, straight-chain or branched alkoxy having 1 to 3 carbon atoms and alkoxycarbonyl having 1 or 2 carbon atoms in the alkoxy part, $R^{2'}$ represents straight-chain or branched alkyl having 1 to 4 carbon atoms, $R^{3'}$ represents straight-chain or branched alkyl having 1 to 4 carbon atoms or straight-chain or branched alkenyl having 3 to 5 carbon atoms, $R^{4'}$ represents straight-chain or branched alkyl having 1 to 4 carbon atoms, and $R^{3'}$ and $R^{4'}$, together with the nitrogen atom to which they are bonded, represent a piperidine, morpholine or pyrrolidine radical which is optionally monosubstituted to trisubstituted by identical or different alkyl radicals having 1 to 3 carbon atoms, as well as those aminoketals of the formula (IA), in which $R^{1'}$ represents the groupings

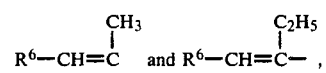

wherein $R^6$ represents phenyl which in each case is optionally monosubstituted to trisubstituted by identical or different substituents, the following being mentioned as substituents: fluorine, chlorine, bromine, nitro, cyclohexyl, straight-chain or branched alkyl or alkoxy, each having 1 to 4 carbon atoms, and alkoxycarbonyl having 1 or 2 carbon atoms in the alkoxy part, $R^{2'}$ represents straight-chain or branched alkyl having 1 to 4 carbon atoms, $R^{3'}$ represents straight-chain or branched alkyl having 1 to 4 carbon atoms or straight-chain or branched alkenyl having 3 to 5 carbon atoms, $R^{4'}$ represents straight-chain or branched alkyl having 1 to 4 carbon atoms, and $R^{3'}$ and $R^{4'}$, together with the nitrogen atom to which they are bonded, represent the piperidine, morpholine or pyrrolidine radical which is optionally monosubstituted to trisubstituted by identical or different alkyl radicals having 1 to 3 carbon atoms.

Formula (II) gives a general definition of the substituted dioxolanes required as starting materials in carrying out the stated process. In this formula, $R^{1'}$ and $R^{2'}$ preferably have those meanings which have already been mentioned in connection with the description of the substances according to the invention, of the formula (IA), as being preferred for these radicals. X preferably represents chlorine, bromine, methanesulphonyloxy, p-toluenesulphonyloxy or triflorome-thanesulfphonyloxy.

Some of the substituted dioxolanes of the formula (II) are known ]see, for example: Rec. Trav. Chim. PaysBas 91, 989-1001 (1972) Farm. Ed. Sci. 29, 167-174, (1974), and J. med. Chem. 6 (1963), 3, 325-328], or can be obtained by processes similar to those described in these references, by reacting, for example, aldehydes or ketones of the formula

in which $R^{1'}$ and $R^{2'}$ have the meaning given above, in a customary manner with substituted 1,2-diols of the formula

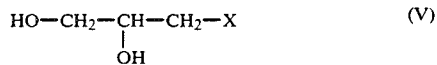

in which X has the meaning given above, in the presence of an inert organic solvent, such as, for example, toluene, and in the presence of a catalyst, such as, for example, p-toluenesulphonic acid, at temperatures between 50° C. and 120° C.

Formula (III) gives a general definition of the amines additionally required as starting materials for the stated process. In this formula, $R^{3'}$ and $R^{4'}$ preferably represent those radicals which have already been mentioned in connection with the description of the substances according to the invention, of the formula (IA), as being preferred by these substituents.

The amines of the formula (III) are generally known compounds of organic chemistry.

Organic solvents are suitable diluents for the process. Such solvents preferably include aromatic hydrocarbons, such as benzene, toluene or xylene; halogenated hydrocarbons, such as carbon tetrachloride or chlorobenzene; formamides such as dimethylformamide; nitriles, such as acetonitrile or propionitrile; alcohols, such as propanol or butanol; amines, such as triethylamine or piperidine; and the highly polar solvents dimethylsulphoxide or hexamethylphosphoric acid triamide. The process is carried out, if appropriate, in the presence of a base as an acid-binding agent. All customary organic and, in particular, inorganic bases can be employed for this purpose. These preferably include alkali metal hydroxides or carbonates, such as, for example, sodium hydroxide, sodium carbonate or potassium carbonate; and also triethylamine and pyridine. If desired, the amines of the formula (III) which are employed as starting materials may also be used as solvents and as acid-binding agents.

The process is carried out, if appropriate, in the presence of a catalyst. Alkali metal iodides, such as, for example, potassium iodide, are preferably used.

In the process, the reaction temperatures can be varied within a relatively wide range. In general, the reaction is carried out at between 50° C. and 250° C., preferably between 80° C. and 200° C.

The process can be carried out under atmospheric pressure or under elevated pressure. In general, the reaction is carried out at pressures between about 1.5 atm and 5 atm, preferably about 1.5 atm and 3 atm.

In carrying out the process, 1 to 30 mols of the amine of the formula (III), depending on whether the amine is also used as a diluent and/or an acid-binding agent, are preferably employed per mol of substituted dioxolane of the formula (II). The isolation of the end products is effected by customary methods.

Suitable anions of the salts are those which are preferably derived from the following acids: hydrohalic acids, such as, for example, hydrochloric acid and hydrobromic acids and also phosphoric acid, nitric acid and sulphuric acid.

The metal salt complexes of compounds of the formula (I) or (IA) can be obtained in a simple manner by customary processes, thus, for example, by dissolving the metal salt in an alcohol, for example ethanol, and adding the solution to the compound of the formula (I) or (IA). Metal salt complexes can be purified in a known manner, for example by filtration, isolating and if appropriate by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the powdery mildew of barley causative organism (*Erysiphe graminis*) of the stripe disease causative organism (*Drechslera graminea*), rice diseases, such as, for example, *Pyricularia oryzae,* or potato diseases, such as, for example, against the potato blight causative organism (Phytophtora infestans).

The active compounds can be converted to the customary formulations, such as solutions, emulsions, suspensions, powders, foams, pastes, granules aerosols, very fine capsules in polymeric substances and in coating compositions for seed and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations as a mixture with other known compounds, such as fungicides, insecticides, acaricides, herebicides, bactericides, nematicides, bird repellents, growth factors, plant nutrients and agents for improving soil structure.

The active compounds can be used as such or in the form of their formulations or the use forms prepared therefrom, such as ready-to-use solutions, emulsifiable concentrates, emulsions, forms, suspensions, wettable powders, pastes, soluble powders, dusting agents and granules. They are used in the customary manner, for example by watering, spraying, atomizing, scattering, dusting, foaming, brushing, etc. It is also possible to apply the active compounds by the ultra-low-volume method, or to inject the formulation of active compound, or the active compound itself, into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

PREPARATION EXAMPLES

EXAMPLE 1

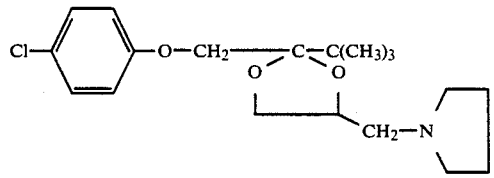

17.3 g (0.05 mol) of 2-(t-butyl)-2-(4-chlorophenoxymethyl)-4-methanesuylphonyloxymethyl-1,3-dioxolane and 7.1 g (0.1 mol) of pyrrolidine are heated at 120° C. for 15 hours. After the mixture has been cooled, excess pyrrolidine is distilled off in vacuo, and the residue is taken up in ether. The ether solution is washed twice with water, dried over sodium sulphate and evaporated down in vacuo.

12.1 g (65.7% of theory) of 2-(t-butyl)-2-(4-chlorophenoxymethyl)-4-(pyrrolidin-1-ylmethyl)-1,3-dioxolane are obtained as an oil of refractive index $n_D$ 1.5099.

Preparation of the starting material

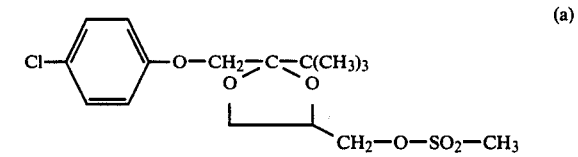

(a)

142 g (0.5 mol) of 2-(t-butyl)-2-(4-chlorophenoxymethyl)-4-hydroxymethyl-1,3-dioxolane are taken up in 150 ml of pyridine and 57 g (0.5 mol) of methanesulphonyl chloride are added dropwise at 0° C. The mixture is stirred for 17 hours at 20° C.-25° C., and the solvent is then distilled off in vacuo. The residue is taken up in ether, and the ether solution is washed with water, dried over sodium sulphate and evaporated down in vacuo.

171 g (98% of theory) of 2-(t-butyl)-2-(4-chlorophenoxymethyl)-4-methanesulphonyloxymethyl-1,3-dioxolane are obtained as an oil.

$^1$H-NMR (CDCl$_3$): δ(ppm)=7.2 (d, 2H), 6.8 (d, 2H), 4.6–3.6 (m, 7H), 3.0 (d, 3H), 1.05 (s, 9H).

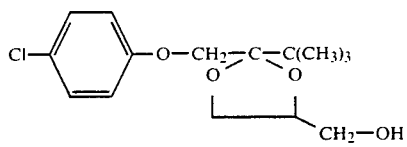

226 g (1 mol) of 1-(4-chlorophenoxy)-3,3-dimethylbutan-2-one (obtained from sodium 4-chlorophenolate and α-bromopinacolone; in this respect, see German Patent Specification No. 2,201,063), together with 120 g (1.07 mols) of glycerol, 19 g (0.1 mol) of p-toluenesulphonic acid monohydrate and 30 ml of butanol, are dissolved in 1,000 ml of toluene, and the mixture is heated under reflux for 16 hours in a water separator. After the mixture has been cooled, the toluene phase is washed with 4 times 250 ml of water, dried over magnesium sulphate, filtered, and evaporated down in vacuo. 186 g (65.4% of theory) of 2-(t-butyl)-2-(4-chlorophenoxymethyl)-4-hydroxymethyl-1,3-dioxolane of boiling point b.p.$_{0.1}$: 161° C.–163° C. are obtained by distillation.

EXAMPLE 2

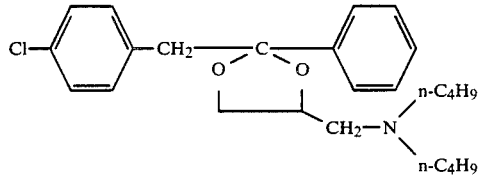

16.1 g (0.05 mol) of 4-chloromethyl-2-(4-chlorophenylmethyl)-2-phenyl-1,3-dioxolane, 100 ml of di-n-butylamine and 13.8 g (0.1 mol) of potassium carbonate together with a pinch of potassium iodide are stirred for 8 hours at 180° C. and 2 bar in an autoclave.

To work up the mixture, the excess di-n-butylamine is removed under vacuum from a water jet, at a bath temperature of 40° C.–100° C. The residue, when it is cold, is taken up in 50 ml of toluene, and the solution is filtered and evaporated down in vacuo.

9.4 g (47% of theory) of 2-(4-chlorophenylmethyl)-4-(N,N-di-n-butylaminomethyl)-2-phenyl-1,3-dioxolane are obtained as an oil of refractive index n$_D^{20}$=1.5172.

Preparation of the starting material

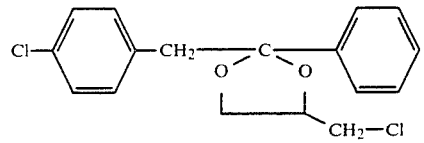

69 g (0.3 mol) of phenyl 4-chlorophenylmethyl ketone, 66.3 g (0.6 mol) of 3-chloropropane-1,2-diol and 5.2 g (0.03 mol) of p-toluenesulphonic acid in 600 ml of toluene are refluxed for three days in a water separator. The reaction mixture, when it is cold, is extracted with sodium bicarbonate solution, dried over sodium sulphate and evaporated down in vacuo. 95 g (98% of theory) of 4-chloromethyl-2-(4-chlorophenylmethyl)-2-phenyl-1,3-dioxolane of melting point 65° C. are obtained.

EXAMPLE 3

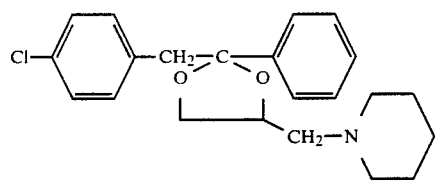

16.1 g (0.05 mol) of 4-chloromethyl-2-(4-chlorophenylmethyl)-2-phenyl-1,3-dioxolane (for the preparation see Example 2), 100 g (1.18 mols) of piperidine, 1.38 g (0.1 mol) of potassium carbonate and a pinch of potassium iodide are boiled under reflux together for 16 hours. The reaction mixture is evaporated down in vacuo, the residue is taken up in 150 ml of 0.4N hydrochloric acid, and the solution is washed 3 times with 50 ml of ligroin. The solution containing hydrochloric acid is saturated with sodium chloride and extracted 3 times with 60 ml of ethyl acetate. The ethyl acetate phase is washed with sodium bicarbonate solution and sodium chloride solution, dried over sodium sulphate, and freed from solvent in vacuo at a bath temperature of 40° C.

10 g (53.8% of theory) of 2-(4-chlorophenylmethyl)-2-phenyl-4-(piperidin-1-ylmethyl)-1,3-dioxolane are obtained as a wax-like solid residue of melting point 58° C.

The following compounds of the formula (I)

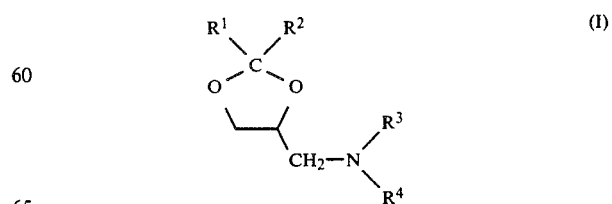

were obtained in a corresponding manner and according to the stated process:

| Example No. | R¹ | R² | $-N\begin{smallmatrix}R^3\\R^4\end{smallmatrix}$ | Melting point (°C.) or refractive index ($n_D^{20}$) |
|---|---|---|---|---|
| 4 | C$_2$H$_5$ | CH$_3$ | $-N(C_4H_9\text{-}n)_2$ | 1.5027 |
| 5 | C$_2$H$_5$ | CH$_3$ | 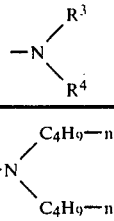 pyrrolidino | 1.5036 |
| 6 | C$_2$H$_5$ | CH$_3$ | 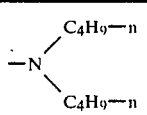 piperidino | 1.5012 |
| 7 | C$_2$H$_5$ | CH$_3$ |  morpholino | 1.5047 |
| 8 | C$_2$H$_5$ | CH$_3$ | 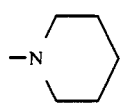 pyrazolyl | 1.4682 |
| 9 | i-C$_4$H$_9$ | CH$_3$ | 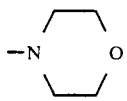 piperidino | 1.5039 |
| 10 | i-C$_4$H$_9$ | CH$_3$ |  morpholino | 1.5041 |
| 11 | i-C$_4$H$_9$ | CH$_3$ | 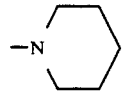 N-methylpiperazino | 1.5035 |
| 12 | n-C$_9$H$_{19}$ | CH$_3$ | 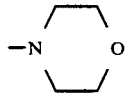 pyrrolidino | 1.4570 |
| 13 | n-C$_9$H$_{19}$ | CH$_3$ | 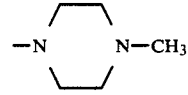 piperidino | 1.4535 |
| 14 | n-C$_9$H$_{19}$ | CH$_3$ |  hexamethyleneimino | 1.4549 |
| 15 | n-C$_9$H$_{19}$ | CH$_3$ | 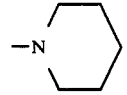 morpholino | 1.4489 |

-continued
| Example No. | $R^1$ | $R^2$ | $-N\begin{matrix}R^3\\R^4\end{matrix}$ | Melting point (°C.) or refractive index ($n_D^{20}$) |
|---|---|---|---|---|
| 16 | n-C₉H₁₉ | CH₃ | 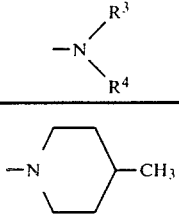 | 1.4510 |
| 17 | n-C₉H₁₉ | CH₃ | 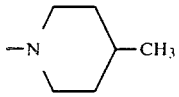 | 1.4551 |
| 18 | n-C₉H₁₉ | n-C₉H₁₉ | 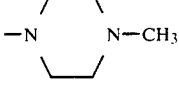 | 1.4510 |
| 19 | n-C₉H₁₉ | n-C₉H₁₉ |  | 1.4588 |
| 20 | n-C₉H₁₉ | n-C₉H₁₉ |  | 1.4578 |
| 21 | n-C₉H₁₉ | n-C₉H₁₉ | 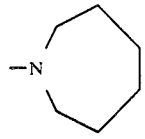 | 1.4539 |
| 22 | n-C₉H₁₉ | n-C₉H₁₉ | 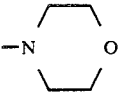 | 1.4534 |
| 23 | n-C₉H₁₉ | n-C₉H₁₉ | 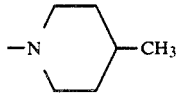 | 1.4555 |
| 24 | 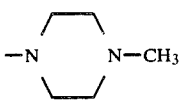 | CH₃ | 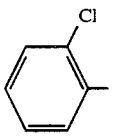 | 1.5301 |
| 25 |  | CH₃ | 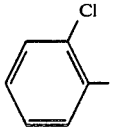 | 1.5326 |
| 26 | 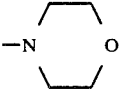 | CH₃ | 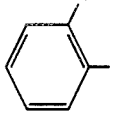 | 1.5084 |

-continued

| Example No. | $R^1$ | $R^2$ | $-N\begin{matrix}R^3\\R^4\end{matrix}$ | Melting point (°C.) or refractive index ($n_D^{20}$) |
|---|---|---|---|---|
| 27 | 2,4-dichlorophenyl- | $CH_3$ | piperidino | 1.5372 |
| 28 | 2,4-dichlorophenyl- | $CH_3$ | 2,6-dimethylmorpholino | 1.5219 |
| 29 | 2,5-dichlorophenyl- | $CH_3$ | piperidino | 1.5383 |
| 30 | 2,5-dichlorophenyl- | $CH_3$ | morpholino | 1.5384 |
| 31 | 2,5-dichlorophenyl- | $CH_3$ | 2,6-dimethylmorpholino | 1.5181 |
| 32 | 4-chlorobenzyl- | $C_6H_5$ | pyrrolidino | 61 |
| 33 | 4-chlorobenzyl- | $C_6H_5$ | 4-methylpiperazino | 71 |
| 34 | 4-Cl-C$_6$H$_4$-CH$_2$-C(CH$_3$)$_2$- | $CH_3$ | pyrrolidino | 1.5261 |
| 35 | 4-Cl-C$_6$H$_4$-CH$_2$-C(CH$_3$)$_2$- | $CH_3$ | piperidino | 1.5244 |
| 36 | 4-Cl-C$_6$H$_4$-O-CH$_2$- | $CH_3$ | piperidino | 1.5282 |

-continued

| Example No. | R¹ | R² | −N(R³)(R⁴) | Melting point (°C.) or refractive index ($n_D^{20}$) |
|---|---|---|---|---|
| 37 | 4-Cl-C₆H₄-O-CH₂- | t-C₄H₉ | −N(C₃H₇-n)(C₃H₇-n) | 1.4889 |
| 38 | 4-Cl-C₆H₄-O-CH₂- | t-C₄H₉ | −N(C₄H₉-i)(C₄H₉-i) | 1.5003 |
| 39 | 4-Cl-C₆H₄-O-CH₂- | t-C₄H₉ | −N(C₆H₁₁)(C₆H₁₁) (dicyclohexylamino) | 98 |
| 40 | 4-Cl-C₆H₄-O-CH₂- | t-C₄H₉ | −N(CH₂-C₆H₅)(CH₂-C₆H₅) | 121 |
| 41 | 4-Cl-C₆H₄-O-CH₂- | t-C₄H₉ | −N(CH₃)(CH₂-C₆H₅) | 1.5049 |
| 42 | 4-Cl-C₆H₄-O-CH₂- | t-C₄H₉ | piperidino | 1.5173 |
| 43 | 4-Cl-C₆H₄-O-CH₂- | t-C₄H₉ | 2-methylpiperidino | 1.5068 |
| 44 | 4-Cl-C₆H₄-O-CH₂- | t-C₄H₉ | 3-methylpiperidino | 1.5026 |
| 45 | 4-Cl-C₆H₄-O-CH₂- | t-C₄H₉ | 4-methylpiperidino | 1.5032 |
| 46 | 4-Cl-C₆H₄-O-CH₂- | t-C₄H₉ | 3,5-dimethylpiperidino | 1.5012 |
| 47 | 4-Cl-C₆H₄-O-CH₂- | t-C₄H₉ | morpholino | 40 |

-continued

| Example No. | R¹ | R² | −N(R³)(R⁴) | Melting point (°C.) or refractive index ($n_D^{20}$) |
|---|---|---|---|---|
| 48 | 4-Cl-C₆H₄-O-CH₂- | t-C₄H₉ | 2,6-dimethylmorpholino | 1.5082 |
| 49 | 4-Cl-C₆H₄-O-CH₂- | t-C₄H₉ | 4-methylpiperazin-1-yl | 1.5187 |
| 50 | 4-Br-C₆H₄-O-CH₂- | t-C₄H₉ | piperidino | 1.5271 |
| 51 | 4-Br-C₆H₄-O-CH₂- | t-C₄H₉ | 2,6-dimethylmorpholino | 1.5126 |
| 52 | 4-F-C₆H₄-O-CH₂- | t-C₄H₉ | pyrrolidin-1-yl | 1.4917 |
| 53 | 4-F-C₆H₄-O-CH₂- | t-C₄H₉ | piperidino | 1.5026 |
| 54 | 4-F-C₆H₄-O-CH₂- | t-C₄H₉ | 2-methylpiperidino | 1.4992 |
| 55 | 4-F-C₆H₄-O-CH₂- | t-C₄H₉ | 3-methylpiperidino | 1.5023 |
| 56 | 4-F-C₆H₄-O-CH₂- | t-C₄H₉ | 4-methylpiperidino | 1.5045 |
| 57 | 4-F-C₆H₄-O-CH₂- | t-C₄H₉ | 3,5-dimethylpiperidino | 1.5008 |

-continued

| Example No. | R¹ | R² | -N(R³)(R⁴) | Melting point (°C.) or refractive index ($n_D^{20}$) |
|---|---|---|---|---|
| 58 | 4-F-C₆H₄-O-CH₂- | t-C₄H₉ | -N(morpholine with 2,6-diCH₃) | 1.4938 |
| 59 | 4-F-C₆H₄-O-CH₂- | t-C₄H₉ | -N(CH₂-C₆H₅)₂ | 134 |
| 60 | 2,6-Cl₂-C₆H₃-O-CH₂- | t-C₄H₉ | -N(piperidine) | 1.5109 |
| 61 | 2,6-Cl₂-C₆H₃-O-CH₂- | t-C₄H₉ | -N(morpholine) | 1.5226 |
| 62 | 3-C₆H₅-C₆H₄-O-CH₂- | t-C₄H₉ | -N(piperidine) | 1.5577 |
| 63 | 3-C₆H₅-C₆H₄-O-CH₂- | t-C₄H₉ | -N(morpholine) | 1.5557 |
| 64 | C₆H₅-O-CH₂-C(CH₃)₃ | CH₃ | -N(piperidine) | 1.5011 |
| 65 | C₆H₅-O-CH₂-C(CH₃)₃ | CH₃ | -N(2-methylpiperidine) | 1.4998 |
| 66 | C₆H₅-O-CH₂-C(CH₃)₃ | CH₃ | -N(3-methylpiperidine) | 1.4973 |
| 67 | C₆H₅-O-CH₂-C(CH₃)₃ | CH₃ | -N(4-methylpiperidine) | 1.4939 |

-continued
| Example No. | R¹ | R² | −N(R³)(R⁴) | Melting point (°C.) or refractive index ($n_D^{20}$) |
|---|---|---|---|---|
| 68 |  | CH₃ | 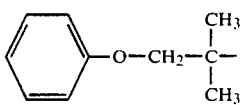 | 1.4974 |
| 69 | 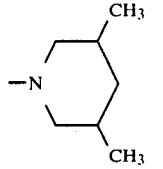 | CH₃ | 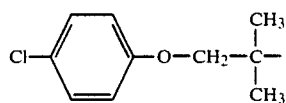 | 1.5200 |
| 70 | 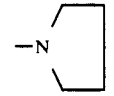 | CH₃ | 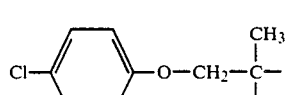 | 1.5121 |
| 71 | 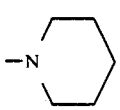 | CH₃ | 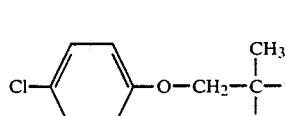 (× HCl) | 153–155 |
| 72 | 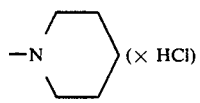 | CH₃ | 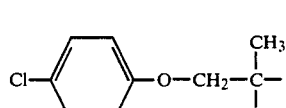 | 1.5102 |
| 73 | 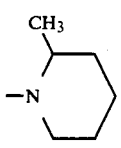 | CH₃ | 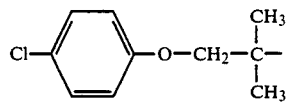 | 1.5431 |
| 74 | 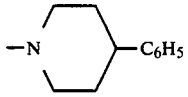 | CH₃ | 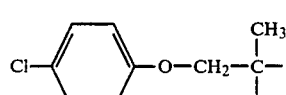 | 1.5191 |
| 75 | 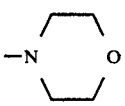 | CH₃ | 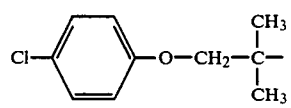 | 1.4993 |
| 76 | 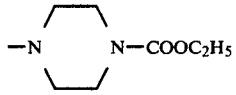 | CH₃ | 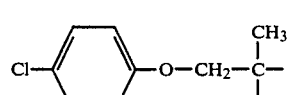 | 1.5377 |
| 77 | 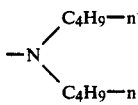 | CH₃ | 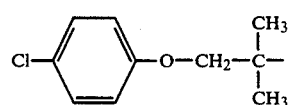 | 1.5150 |
| 78 | 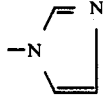 | CH₃ | 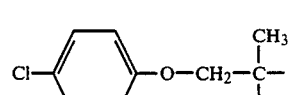 | 100 (× HCl) |

| Example No. | R¹ | R² | -N(R³)(R⁴) | Melting point (°C) or refractive index ($n_D^{20}$) |
|---|---|---|---|---|
| 79 | 2-Cl-C₆H₄-O-CH₂-C(CH₃)₂- | CH₃ | 2-methylpiperidin-1-yl | 1.5047 |
| 80 | 2-Cl-C₆H₄-O-CH₂-C(CH₃)₂- | CH₃ | 3-methylpiperidin-1-yl | 1.5051 |
| 81 | 2,4-Cl₂-C₆H₃-O-CH₂-C(CH₃)₂- | CH₃ | piperidin-1-yl | 1.5006 |
| 82 | 2,4-Cl₂-C₆H₃-O-CH₂-C(CH₃)₂- | CH₃ | 2-methylpiperidin-1-yl | 1.4941 |
| 83 | 2,4-Cl₂-C₆H₃-O-CH₂-C(CH₃)₂- | CH₃ | 3-methylpiperidin-1-yl | 1.5034 |
| 84 | 2,4-Cl₂-C₆H₃-O-CH₂-C(CH₃)₂- | CH₃ | 4-methylpiperidin-1-yl | 1.4987 |
| 85 | 2,4-Cl₂-C₆H₃-O-CH₂-C(CH₃)₂- | CH₃ | 3,5-dimethylpiperidin-1-yl | 1.4980 |
| 86 | 2,4-Cl₂-C₆H₃-O-CH₂-C(CH₃)₂- | CH₃ | 2,4-dimethylpiperidin-1-yl | 1.5021 |
| 87 | 2,4-Cl₂-C₆H₃-O-CH₂-C(CH₃)₂- | CH₃ | 2,6-dimethylpiperidin-1-yl | 1.4980 |

-continued

| Example No. | R¹ | R² | −N(R³)(R⁴) | Melting point (°C.) or refractive index ($n_D^{20}$) |
|---|---|---|---|---|
| 88 | 2,4-dichlorophenyl-O-CH₂-C(CH₃)₂- | CH₃ | 2,6-dimethylmorpholino | 1.5034 |
| 89 | 2-methylphenyl-O-CH₂-C(CH₃)₂- | CH₃ | piperidino | 1.4952 |
| 90 | 4-chloro-2-methylphenyl-O-CH₂-C(CH₃)₂- | CH₃ | 2,6-dimethylmorpholino | 1.4874 |
| 91 | 3-methylphenyl-O-CH₂-C(CH₃)₂- | CH₃ | 4-methylpiperazin-1-yl | 1.5023 |
| 92 | 4-methylphenyl-O-CH₂-C(CH₃)₂- | CH₃ | −N(n-C₄H₉)₂ | 1.5132 |
| 93 | 4-methylphenyl-O-CH₂-C(CH₃)₂- | CH₃ | hexamethyleneimino | 1.5118 |
| 94 | 2,4-dimethylphenyl-O-CH₂-C(CH₃)₂- | CH₃ | pyrrolidino | 1.5081 |
| 95 | 2,4-dimethylphenyl-O-CH₂-C(CH₃)₂- | CH₃ | piperidino | 1.5064 |
| 96 | 2,4-dimethylphenyl-O-CH₂-C(CH₃)₂- | CH₃ | 4-methylpiperazin-1-yl | 1.5086 |

-continued

| Example No. | R¹ | R² | −N(R³)(R⁴) | Melting point (°C.) or refractive index ($n_D^{20}$) |
|---|---|---|---|---|
| 97 | 2,4,6-trimethylphenyl−O−CH₂−C(CH₃)₃ | CH₃ | pyrrolidin-1-yl | 1.5087 |
| 98 | 2,6-dimethylphenyl−O−CH₂−C(CH₃)₃ | CH₃ | piperidin-1-yl | 1.5074 |
| 99 | 2,6-dimethylphenyl−O−CH₂−C(CH₃)₃ | CH₃ | 4-methylpiperazin-1-yl | 1.5067 |
| 100 | 2-methoxyphenyl−O−CH₂−C(CH₃)₃ | CH₃ | −N(n-C₄H₉)₂ | 1.5063 |
| 101 | 2-methoxyphenyl−O−CH₂−C(CH₃)₃ | CH₃ | pyrrolidin-1-yl | 1.5057 |
| 102 | 2-methoxyphenyl−O−CH₂−C(CH₃)₃ | CH₃ | piperidin-1-yl | 1.5070 |
| 103 | 2-methoxyphenyl−O−CH₂−C(CH₃)₃ | CH₃ | 3,5-dimethylpiperidin-1-yl | 1.4944 |
| 104 | 2-methoxyphenyl−O−CH₂−C(CH₃)₃ | CH₃ | morpholin-4-yl | 1.5067 |
| 105 | 2-ethylphenyl−O−CH₂−C(CH₃)₃ | CH₃ | piperidin-1-yl | 1.5087 |

-continued

| Example No. | R¹ | R² | −N(R³)(R⁴) | Melting point (°C.) or refractive index ($n_D^{20}$) |
|---|---|---|---|---|
| 106 | 2-C₂H₅-C₆H₄-O-CH₂-C(CH₃)₂- | CH₃ | morpholino | 1.5076 |
| 107 | 2-C₂H₅-C₆H₄-O-CH₂-C(CH₃)₂- | CH₃ | 4-methylpiperazin-1-yl | 1.5046 |
| 108 | 4-t-C₄H₉-C₆H₄-O-CH₂-C(CH₃)₂- | CH₃ | pyrrolidin-1-yl | 1.4948 |
| 109 | 4-t-C₄H₉-C₆H₄-O-CH₂-C(CH₃)₂- | CH₃ | piperidin-1-yl | 1.4954 |
| 110 | 4-t-C₄H₉-C₆H₄-O-CH₂-C(CH₃)₂- | CH₃ | morpholino | 1.4962 |
| 111 | 4-t-C₄H₉-C₆H₄-O-CH₂-C(CH₃)₂- | CH₃ | 4-methylpiperazin-1-yl | 1.4975 |
| 112 | 4-c-C₆H₁₁-C₆H₄-O-CH₂-C(CH₃)₂- | CH₃ | pyrrolidin-1-yl | 1.5110 |
| 113 | 4-c-C₆H₁₁-C₆H₄-O-CH₂-C(CH₃)₂- | CH₃ | piperidin-1-yl | 1.5098 |
| 114 | C₆H₅-O-CH₂-C(CH₃)₂- | CH₃ | 4-methylpiperazin-1-yl | 1.5031 |
| 115 | C₆H₅-O-CH₂-C(CH₃)₂- | CH₃ | 2,6-dimethylmorpholino | 1.4925 |
| 116 | 2-Cl-C₆H₄-O-CH₂-C(CH₃)₂- | CH₃ | 4-methylpiperidin-1-yl | 1.5044 |

-continued
| Example No. | R¹ | R² | −N(R³)(R⁴) | Melting point (°C.) or refractive index ($n_D^{20}$) |
|---|---|---|---|---|
| 117 | 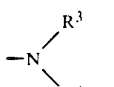 | CH₃ | 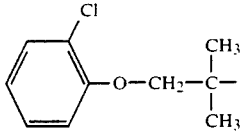 | 1.5047 |
| 118 | 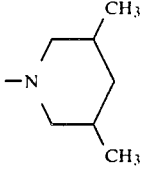 | CH₃ | 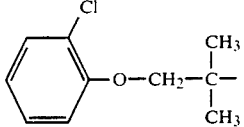 | 1.5040 |
| 119 | 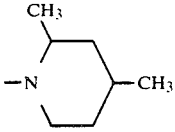 | CH₃ | 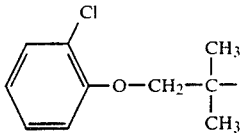 | 1.5044 |
| 120 | 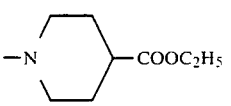 | CH₃ | 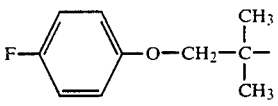 | 1.4912 |
| 121 | 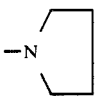 | CH₃ | 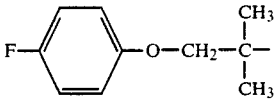 | 1.4907 |
| 122 | 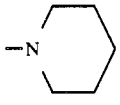 | CH₃ | 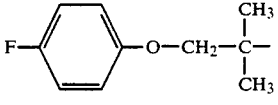 | 1.4930 |
| 123 | 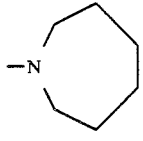 | CH₃ | 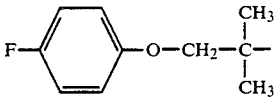 | 1.4868 |
| 124 | 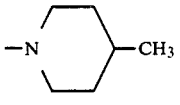 | CH₃ | 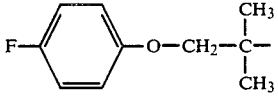 | 1.4873 |
| 125 | 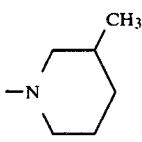 | CH₃ | 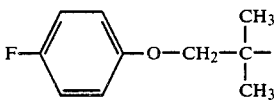 | 1.4897 |
| 126 | 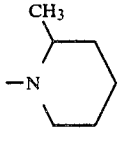 | CH₃ | 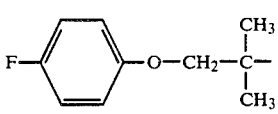 | 1.4841 |

-continued

| Example No. | R¹ | R² | $-N\begin{smallmatrix}R^3\\R^4\end{smallmatrix}$ | Melting point (°C.) or refractive index ($n_D^{20}$) |
|---|---|---|---|---|
| 127 | 4-F-C₆H₄-O-CH₂-C(CH₃)₂- | CH₃ | 2,6-dimethylpiperidin-1-yl | 1.4893 |
| 128 | 4-F-C₆H₄-O-CH₂-C(CH₃)₂- | CH₃ | 2,4-dimethylpiperidin-1-yl | 1.4864 |
| 129 | 4-F-C₆H₄-O-CH₂-C(CH₃)₂- | CH₃ | 3,3-dimethylpiperidin-1-yl | 1.4825 |
| 130 | 4-F-C₆H₄-O-CH₂-C(CH₃)₂- | CH₃ | 4-phenylpiperidin-1-yl | 1.5118 |
| 131 | 4-F-C₆H₄-O-CH₂-C(CH₃)₂- | CH₃ | 2,6-dimethylmorpholin-4-yl | 1.4839 |
| 132 | 4-F-C₆H₄-O-CH₂-C(CH₃)₂- | CH₃ | 4-methylpiperazin-1-yl | 1.4919 |
| 133 | 4-Cl-C₆H₄-O-CH₂-C(CH₃)₂- | CH₃ | 2,6-dimethylmorpholin-4-yl | 1.5361 |
| 134 | 4-Cl-C₆H₄-CH₂- | 4-F-C₆H₄- | $-N(C_4H_9\text{-}n)_2$ | 1.5214 |
| 135 | 4-Cl-C₆H₄-CH₂- | 4-F-C₆H₄- | $-N(C_3H_7\text{-}n)_2$ | 1.5148 |
| 136 | 4-Cl-C₆H₄-CH=CH- | C(CH₃)₃ | 4-methylpiperazin-1-yl | 1.5298 |

-continued
| Example No. | R¹ | R² | −N(R³)(R⁴) | Melting point (°C.) or refractive index ($n_D^{20}$) |
|---|---|---|---|---|
| 137 | 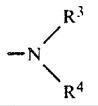 | C(CH₃)₃ | 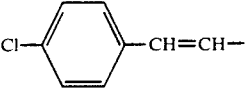 | 74 |
| 138 | 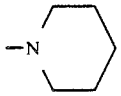 | C(CH₃)₃ | 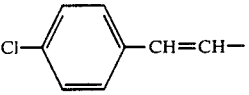 | 86–87 |
| 139 | 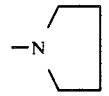 | H | 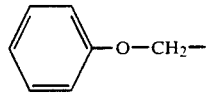 | 1.5222 |
| 140 | 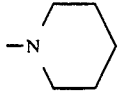 | CH₃ | 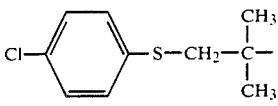 | 1.5491 |
| 141 | 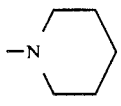 | CH₃ | 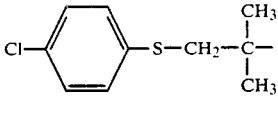 | 1.5626 |
| 142 | 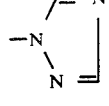 | CH₃ | 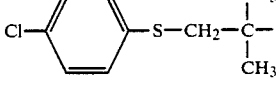 | 1.5538 |
| 143 | 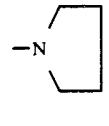 | C(CH₃)₃ | 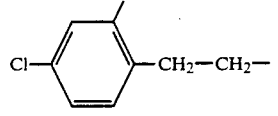 | 1.5171 |
| 144 | 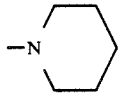 | CH₃ | 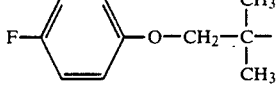 | 1.4968 |
| 145 | 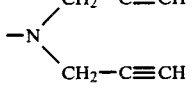 | 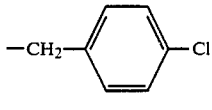 | 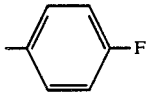 | 1.5498 |
| 146 | 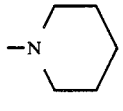 | CH₃ | 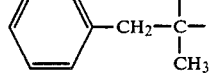 | 1.5091 |
| 147 | 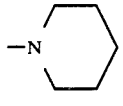 | −C(CH₃)₃ | 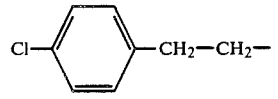 | 1.5179 |
| 148 | 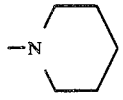 | −C(CH₃)₃ | 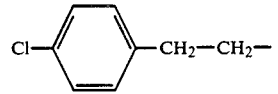 | 117 |

-continued

| Example No. | R¹ | R² | -N<R³R⁴ | Melting point (°C.) or refractive index (n_D^20) |
|---|---|---|---|---|
| 149 | 4-Cl-C₆H₄-SO₂-CH₂-C(CH₃)₂-CH₃ | CH₃ | -N(N=CH-N=CH-) (1,2,4-triazol-1-yl) | 1.5187 |
| 150 | 4-Cl-C₆H₄-SO₂-CH₂-C(CH₃)₂-CH₃ | CH₃ | piperidin-1-yl | 1.5231 |
| 151 | 4-Cl-C₆H₄-O-CH₂-C(CH₃)₂- | 4-Cl-C₆H₄- | 1,2,4-triazol-1-yl | 1.5518 |
| 152 | 4-Cl-C₆H₄-O-CH₂-C(CH₃)₂- | 4-Cl-C₆H₄- | piperidin-1-yl | 1.5518 |
| 153 | 4-Cl-C₆H₄-CH₂- | C₆H₅- | pyrazol-1-yl | 1.5641 |
| 154 | 3-Cl-C₆H₄-CH=CH- | CH₃ | piperidin-1-yl | 1.5366 |
| 155 | C₆H₅-O-CH₂- | H | 1,2,4-triazol-1-yl | 1.5409 |
| 156 | CH₃-C(CH₂F)₂-CH₃ (1,3-difluoro-2-methylpropan-2-yl) | CH₃ | 1,2,4-triazol-1-yl | 30 |
| 157 | CH₃-C(CH₂F)₂-CH₃ | CH₃ | piperidin-1-yl | 1.4599 |
| 158 | 4-Cl-C₆H₄-CH₂-CH(CH₃)- | CH₃ | piperidin-1-yl | 1.5195 |
| 159 | 4-Cl-C₆H₄-CH₂-CH(CH₃)- | CH₃ | 1,2,4-triazol-1-yl | 1.5361 |
| 160 | 2,4-Cl₂-C₆H₃-CH₂-CH₂- | t-C₄H₉ | 1,2,4-triazol-1-yl | 1.5366 |

-continued

| Example No. | R¹ | R² | -N(R³)(R⁴) | Melting point (°C.) or refractive index ($n_D^{20}$) |
|---|---|---|---|---|
| 161 | 3-Cl-C₆H₄- | i-C₄—H₉ | 1H-1,2,4-triazol-1-yl | 1.5263 |
| 162 | 3-Cl-C₆H₄- | i-C₄H₉ | piperidin-1-yl | 1.5179 |
| 163 | C₆H₅—S—CH₂—C(CH₃)₂— | CH₃ | piperidin-1-yl | 1.5445 |
| 164 | C₆H₅—S—CH₂—C(CH₃)₂— | CH₃ | 1H-1,2,4-triazol-1-yl | 1.5568 |
| 165 | CH₃—(CH₂)₈— | CH₃ | —N[(CH₂)₃—CH₃]₂ | 1.4461 |
| 166 | CH₃—(CH₂)₈— | CH₃—(CH₂)₈— | —N[(CH₂)₃—CH₃]₂ | 01 |
| 167 | 4-F-C₆H₄—O—CH₂—C(CH₃)₂— | CH₃ | —N[(CH₂)₃—CH₃]₂ | 1.4702 |
| 168 | 4-F-C₆H₄—O—CH₂—C(CH₃)₂— | CH₃ | morpholin-4-yl | 1.4921 |
| 169 | 2,3,5-(CH₃)₃-C₆H₂—O—CH₂—C(CH₃)₂— | CH₃ | 4-methylpiperidin-1-yl | 1.5019 |
| 170 | 2,3,5-(CH₃)₃-C₆H₂—O—CH₂—C(CH₃)₂— | CH₃ | morpholin-4-yl | 1.5034 |
| 171 | 4-Cl-C₆H₄—O—CH₂—C(CH₃)₂— | CH₃ | 3-methylpiperidin-1-yl | 1.5045 |

-continued
| Example No. | R¹ | R² | −N(R³)(R⁴) | Melting point (°C.) or refractive index ($n_D^{20}$) |
|---|---|---|---|---|
| 172 |  | CH₃ | 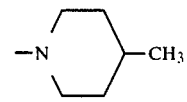 | 1.5040 |
| 173 |  | CH₃ | 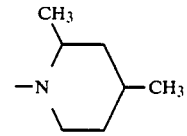 | 1.5031 |
| 174 |  | CH₃ | 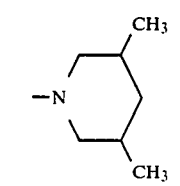 | 1.5000 |
| 175 |  | CH₃ | 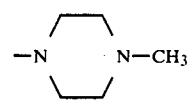 | 1.5082 |
| 176 |  | CH₃ | 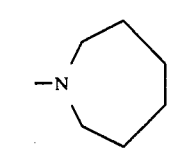 | 1.5079 |
| 177 | 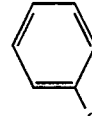 | CH₃ | 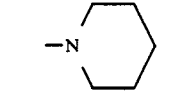 | 1.5087 |
| 178 | 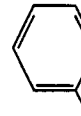 | CH₃ | 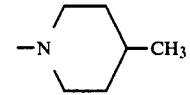 | 1.5095 |
| 179 | 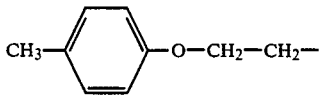 | CH₃ | 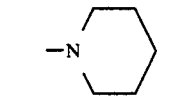 | 1.5117 |
| 180 |  | CH₃ | 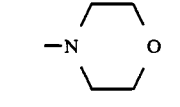 | 1.5060 |
| 181 | 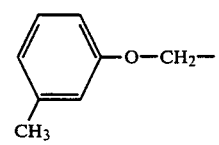 | t-C₄H₉ | 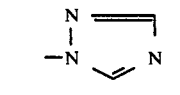 | 1.5072 |

-continued

| Example No. | R¹ | R² | -N(R³)(R⁴) | Melting point (°C.) or refractive index ($n_D^{20}$) |
|---|---|---|---|---|
| 182 | 2-Cl-C₆H₄-CH₂-C(CH₃)₂- | CH₃ | piperidino | 1.5239 |
| 183 | 2-Cl-C₆H₄-CH₂-CH₂- | CH₃ | piperidino | 1.5212 |
| 184 | 2-Cl-C₆H₄-CH₂-CH₂- | CH₃ | 1,2,4-triazol-1-yl | 1.5299 |
| 185 | 3-Cl-C₆H₄-CH₂-CH₂- | CH₃ | piperidino | 1.5282 |
| 186 | 3-Cl-C₆H₄-CH₂-CH₂- | CH₃ | 1,2,4-triazol-1-yl | 1.5386 |
| 187 | 4-Cl-C₆H₄-CH₂-CH(CH₃)- | CH₃ | 4-phenylpiperidino (-C₆H₅) | 1.5506 |
| 188 | C₆H₅-C(CH₃)₂-CH₂- | CH₃ | piperidino | 1.5149 |
| 189 | 2-F-C₆H₄-CH₂-C(CH₃)₂- | CH₃ | pyrrolidino | 1.5086 |
| 190 | 2-F-C₆H₄-CH₂-C(CH₃)₂- | CH₃ | piperidino | 1.5077 |
| 191 | 2-F-C₆H₄-CH₂-C(CH₃)₂- | CH₃ | hexamethyleneimino | 1.5108 |

-continued

| Example No. | $R^1$ | $R^2$ | $-N\begin{smallmatrix}R^3\\R^4\end{smallmatrix}$ | Melting point (°C.) or refractive index ($n_D^{20}$) |
|---|---|---|---|---|
| 192 | 2-F-C$_6$H$_4$-CH$_2$-C(CH$_3$)$_2$-CH$_3$ | CH$_3$ | 2-methylpiperidin-1-yl | 1.5070 |
| 193 | 2-F-C$_6$H$_4$-CH$_2$-C(CH$_3$)$_2$-CH$_3$ | CH$_3$ | 3-methylpiperidin-1-yl | 1.5028 |
| 194 | 2-F-C$_6$H$_4$-CH$_2$-C(CH$_3$)$_2$-CH$_3$ | CH$_3$ | 4-methylpiperidin-1-yl | 1.5035 |
| 195 | 2-F-C$_6$H$_4$-CH$_2$-C(CH$_3$)$_2$-CH$_3$ | CH$_3$ | 3,5-dimethylpiperidin-1-yl | 1.4978 |
| 196 | 4-F-C$_6$H$_4$-CH$_2$-C(CH$_3$)$_2$-CH$_3$ | CH$_3$ | pyrrolidin-1-yl | 1.5069 |
| 197 | 4-F-C$_6$H$_4$-CH$_2$-C(CH$_3$)$_2$-CH$_3$ | CH$_3$ | piperidin-1-yl | 1.5061 |
| 198 | 4-F-C$_6$H$_4$-CH$_2$-C(CH$_3$)$_2$-CH$_3$ | CH$_3$ | hexamethyleneimin-1-yl | 1.5086 |
| 199 | 4-F-C$_6$H$_4$-CH$_2$-C(CH$_3$)$_2$-CH$_3$ | CH$_3$ | 2-methylpiperidin-1-yl | 1.4929 |
| 200 | 4-F-C$_6$H$_4$-CH$_2$-C(CH$_3$)$_2$-CH$_3$ | CH$_3$ | 3-methylpiperidin-1-yl | 1.5018 |
| 201 | 4-F-C$_6$H$_4$-CH$_2$-C(CH$_3$)$_2$-CH$_3$ | CH$_3$ | 4-methylpiperidin-1-yl | 1.5003 |

-continued

| Example No. | R¹ | R² | −N(R³)(R⁴) | Melting point (°C.) or refractive index ($n_D^{20}$) |
|---|---|---|---|---|
| 202 | 4-F-C₆H₄-CH₂-C(CH₃)₂- | CH₃ | 3,5-dimethylpiperidin-1-yl | 1.4952 |
| 203 | 4-F-C₆H₄-CH₂-C(CH₃)₂- | CH₃ | 4-benzylpiperidin-1-yl | 1.5356 |
| 204 | 2-Cl-C₆H₄-CH₂-C(CH₃)₂- | CH₃ | hexamethyleneimin-1-yl | 1.5272 |
| 205 | 2-Cl-C₆H₄-CH₂-C(CH₃)₂- | CH₃ | 2-methylpiperidin-1-yl | 1.5241 |
| 206 | 2-Cl-C₆H₄-CH₂-C(CH₃)₂- | CH₃ | 3-methylpiperidin-1-yl | 130 |
| 207 | 2-Cl-C₆H₄-CH₂-C(CH₃)₂- | CH₃ | 4-methylpiperidin-1-yl | 1.5193 |
| 208 | 2-Cl-C₆H₄-CH₂-C(CH₃)₂- | CH₃ | 2,6-dimethylpiperidin-1-yl | 1.5375 |
| 209 | 2-Cl-C₆H₄-CH₂-C(CH₃)₂- | CH₃ | 3,5-dimethylpiperidin-1-yl | 1.5162 |
| 210 | 2-Cl-C₆H₄-CH₂-C(CH₃)₂- | CH₃ | imidazol-1-yl | 1.5321 |

-continued

| Example No. | R¹ | R² | -N(R³)(R⁴) | Melting point (°C.) or refractive index ($n_D^{20}$) |
|---|---|---|---|---|
| 211 | 2-Cl-C₆H₄-CH₂-C(CH₃)₂- | CH₃ | 1H-1,2,4-triazol-1-yl | 1.5257 |
| 212 | 4-Cl-C₆H₄-CH₂-C(CH₃)₂- | CH₃ | hexahydro-1H-azepin-1-yl | 1.5269 |
| 213 | 4-Cl-C₆H₄-CH₂-C(CH₃)₂- | CH₃ | 2-methylpiperidin-1-yl | 1.5209 |
| 214 | 4-Cl-C₆H₄-CH₂-C(CH₃)₂- | CH₃ | 3-methylpiperidin-1-yl | 1.5185 |
| 215 | 4-Cl-C₆H₄-CH₂-C(CH₃)₂- | CH₃ | 4-methylpiperidin-1-yl | 1.5170 |
| 216 | 4-Cl-C₆H₄-CH₂-C(CH₃)₂- | CH₃ | 3,5-dimethylpiperidin-1-yl | 1.5034 |
| 217 | 4-Cl-C₆H₄-CH₂-C(CH₃)₂- | CH₃ | 3,3-dimethylpiperidin-1-yl | 1.5154 |
| 218 | 4-F-C₆H₄-O-C(CH₃)₂- | CH₃ | hexahydro-1H-azepin-1-yl | — |
| 219 | 4-Cl-C₆H₄-CH₂-C(CH₃)₂- | CH₃ | hexahydro-1H-azepin-1-yl | 1.5341 |

-continued
| Example No. | R¹ | R² | −N(R³)(R⁴) | Melting point (°C.) or refractive index ($n_D^{20}$) |
|---|---|---|---|---|
| 220 | 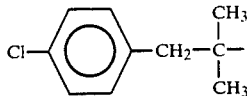 | CH₃ | 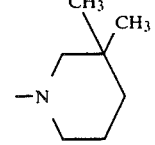 | 1.5249 |
| 221 | 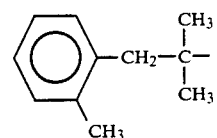 | CH₃ | 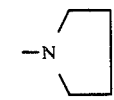 | 1.5189 |
| 222 | 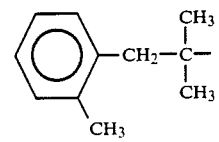 | CH₃ | 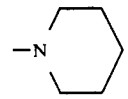 | 1.5177 |
| 223 | 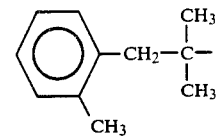 | CH₃ | 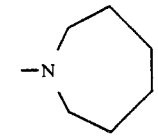 | 1.5189 |
| 224 | 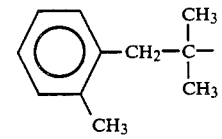 | CH₃ | 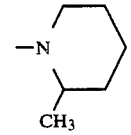 | 1.5177 |
| 225 | 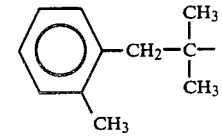 | CH₃ | 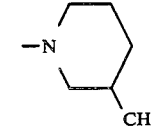 | 1.5178 |
| 226 | 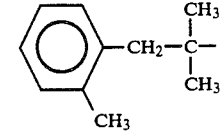 | CH₃ | 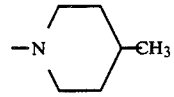 | 1.5126 |
| 227 | 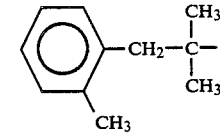 | CH₃ | 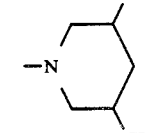 | 1.5091 |
| 228 | 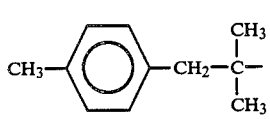 | CH₃ |  | 170 |

-continued

| # | Aryl group | R | Amine | Value |
|---|---|---|---|---|
| 229 | 4-CH₃-C₆H₄-CH₂-C(CH₃)₂- | CH₃ | azepan-1-yl (7-membered N ring) | 1.5170 |
| 230 | 4-CH₃-C₆H₄-CH₂-C(CH₃)₂- | CH₃ | 2-methylpiperidin-1-yl | 1.5032 |
| 231 | 4-CH₃-C₆H₄-CH₂-C(CH₃)₂- | CH₃ | 3-methylpiperidin-1-yl | 1.5111 |
| 232 | 4-CH₃-C₆H₄-CH₂-C(CH₃)₂- | CH₃ | 4-methylpiperidin-1-yl | 1.5105 |
| 233 | 4-CH₃-C₆H₄-CH₂-C(CH₃)₂- | CH₃ | 3,5-dimethylpiperidin-1-yl | 1.5072 |
| 234 | 4-CH₃-C₆H₄-CH₂-C(CH₃)₂- | CH₃ | 3,3-dimethylpiperidin-1-yl | 1.5049 |
| 235 | 4-CH₃-C₆H₄-CH₂-C(CH₃)₂- | CH₃ | imidazol-1-yl | b.p. 160° C./0.1 |
| 236 | 2,4-Cl₂-C₆H₃-O-CH₂- | H | piperidin-1-yl | 1.5433 |
| 237 | 2,4-Cl₂-C₆H₃-O-CH₂- | H | 1,2,4-triazol-1-yl | 1.5601 |
| 238 | 4-F-C₆H₄-O-C(CH₃)₂- | CH₃ | 3-methylpiperidin-1-yl | b.p. 200° C./0.3 |
| 239 | 4-F-C₆H₄-O-C(CH₃)₂- | CH₃ | 3,5-dimethylpiperidin-1-yl | b.p. 190° C./0.2 |

-continued
| | | | | |
|---|---|---|---|---|
| 240 | 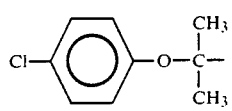 | CH₃ | 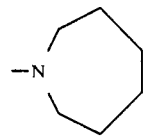 | 1.5092 |
| 241 | 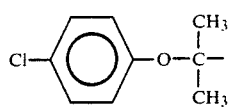 | CH₃ | 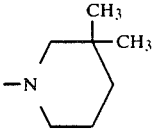 | 1.5062 |
| 242 | 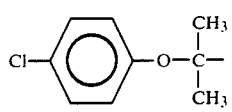 | CH₃ | 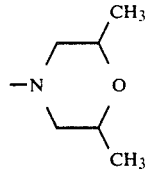 | 1.5076 |
| 243 | 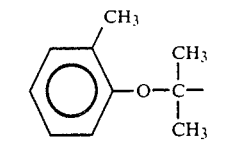 | CH₃ | 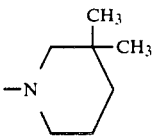 | 1.5039 |
| 244 | 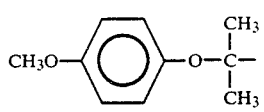 | CH₃ | 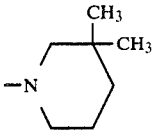 | 1.5047 |
| 245 | 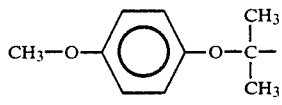 | CH₃ | 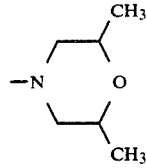 | 1.5067 |
| 246 | 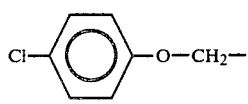 | C(CH₃)₃ | 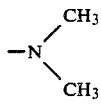 | 1.5042 |
| 247 | 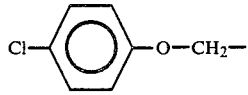 | C(CH₃)₃ | 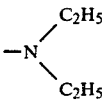 | 1.4987 |
| 248 | 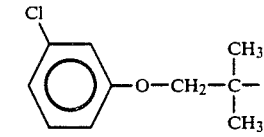 | CH₃ | 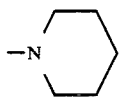 | 1.5073 |
| 249 | 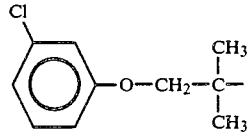 | CH₃ | 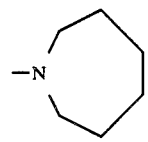 | 1.4995 |
| 250 | 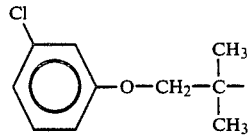 | CH₃ | 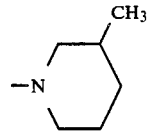 | 1.5073 |

-continued
| | | | | |
|---|---|---|---|---|
| 251 | 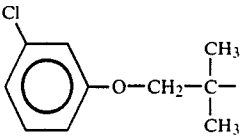 | CH₃ | 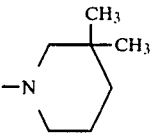 | 1.4995 |
| 252 | 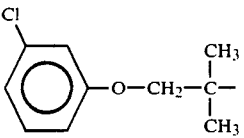 | CH₃ | 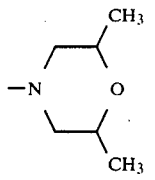 | 1.4970 |
| 253 | 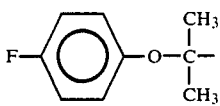 | CH₃ | 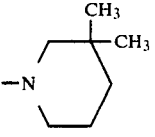 | |
| 254 | 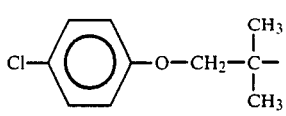 | CH₃ | 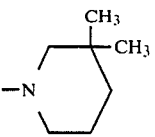 | 1.5105 |
| 255 | 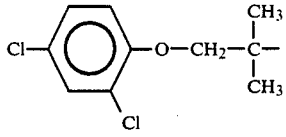 | CH₃ |  | 1.5016 |
| 256 | 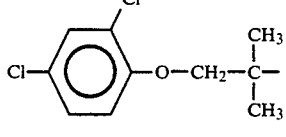 | CH₃ | 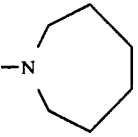 | 1.5076 |
| 257 | 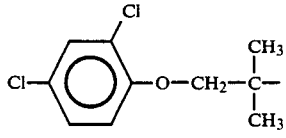 | CH₃ | 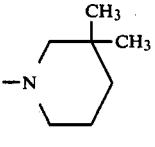 | 1.5044 |
| 258 | 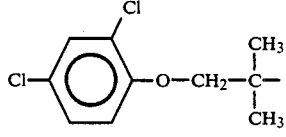 | CH₃ | 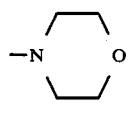 | 1.5064 |
| 259 | 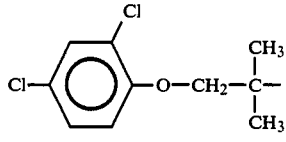 | CH₃ | 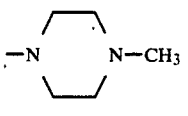 | 1.5023 |
| 260 | 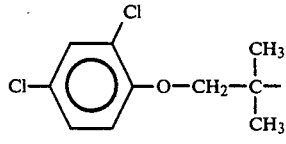 | CH₃ | 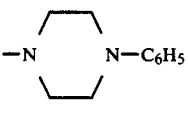 | 1.5092 |
| 261 | 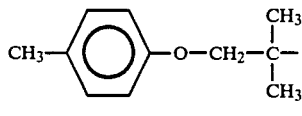 | CH₃ | 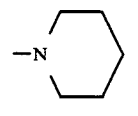 | oil |

-continued
| | | | | |
|---|---|---|---|---|
| 262 | 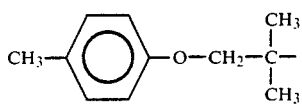 | CH$_3$ | 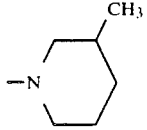 | oil |
| 263 | 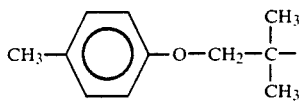 | CH$_3$ | 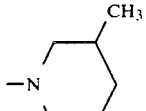 | oil |
| 264 | 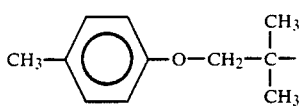 | CH$_3$ | 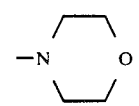 | oil |
| 265 | 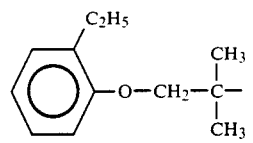 | CH$_3$ | 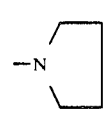 | 1.5110 |
| 266 | 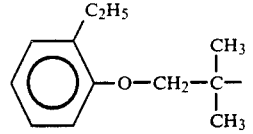 | CH$_3$ | 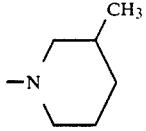 | 1.5042 |
| 267 | 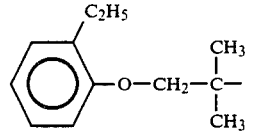 | CH$_3$ | 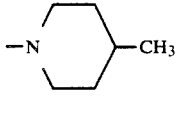 | 1.5067 |
| 268 | 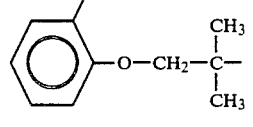 | CH$_3$ | 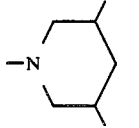 | 1.5047 |
| 269 | 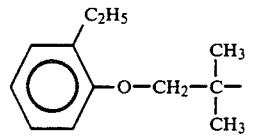 | CH$_3$ | 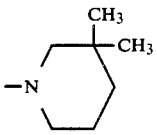 | 1.5071 |
| 270 | 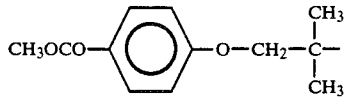 | CH$_3$ | 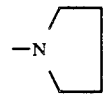 | 1.5085 |
| 271 | 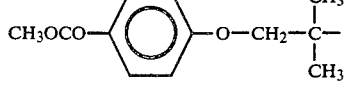 | CH$_3$ | 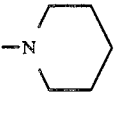 | 1.5043 |
| 272 | 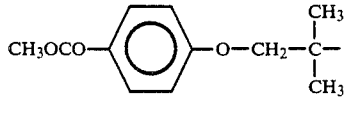 | CH$_3$ | 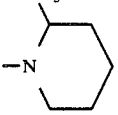 | 1.5061 |

| No. | Ar-O-CH₂-C(CH₃)₂- group | R | Amine | n_D or b.p. |
|---|---|---|---|---|
| 273 | CH₃OCO-C₆H₄-O-CH₂-C(CH₃)₂- | CH₃ | 3-methylpiperidine | 1.5039 |
| 274 | CH₃OCO-C₆H₄-O-CH₂-C(CH₃)₂- | CH₃ | 4-methylpiperidine | 1.5049 |
| 275 | CH₃OCO-C₆H₄-O-CH₂-C(CH₃)₂- | CH₃ | 3,5-dimethylpiperidine | 1.5064 |
| 276 | CH₃OCO-C₆H₄-O-CH₂-C(CH₃)₂- | CH₃ | 2,4-dimethylpiperidine | 1.5051 |
| 277 | CH₃OCO-C₆H₄-O-CH₂-C(CH₃)₂- | CH₃ | 3,3-dimethylpiperidine | 1.5047 |
| 278 | CH₃OCO-C₆H₄-O-CH₂-C(CH₃)₂- | CH₃ | 2,6-dimethylmorpholine | 1.5067 |
| 279 | 4-Cl-2-CH₃-C₆H₃-O-C(CH₃)₂- | CH₃ | 3-methylpiperidine | b.p. 210° C./0.1 |
| 280 | 4-Cl-2-CH₃-C₆H₃-O-C(CH₃)₂- | CH₃ | 3,5-dimethylpiperidine | b.p. 210° C./0.2 |
| 281 | 4-CH₃S-2-CH₃-C₆H₃-O-C(CH₃)₂- | CH₃ | 3-methylpiperidine | 1.5027 |
| 282 | 4-CH₃S-2-CH₃-C₆H₃-O-C(CH₃)₂- | CH₃ | 3,5-dimethylpiperidine | 1.5041 |

-continued
| | | | | |
|---|---|---|---|---|
| 283 | 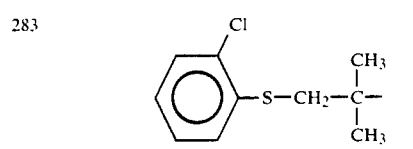 | CH₃ | 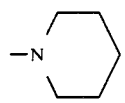 | 1.5422 |
| 284 | 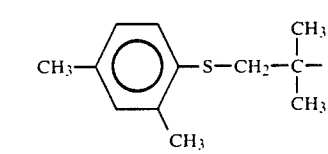 | CH₃ | 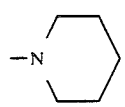 | 1.5457 |
| 285 | 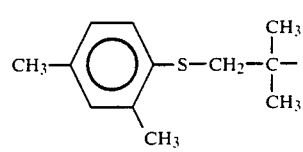 | CH₃ | 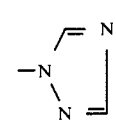 | 1.5305 |
| 286 | 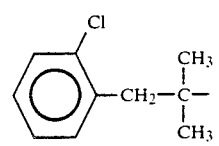 | CH₃ | 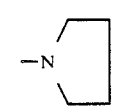 | 1.5269 |
| 287 | 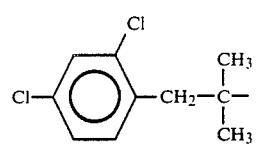 | CH₃ | 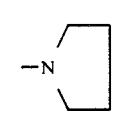 | 1.5346 |
| 288 | 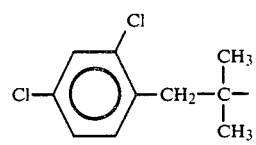 | CH₃ | 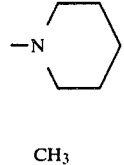 | 1.5340 |
| 289 | 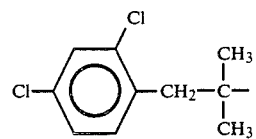 | CH₃ | 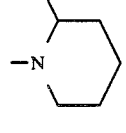 | b.p. 220° C./0.2 |
| 290 | 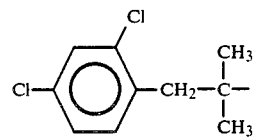 | CH₃ | 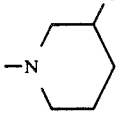 | 1.5293 |
| 291 | 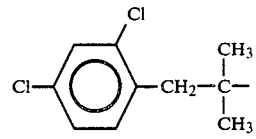 | CH₃ | 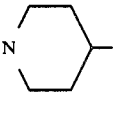 | 1.5286 |
| 292 | 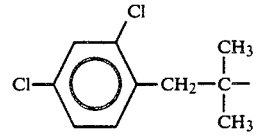 | CH₃ | 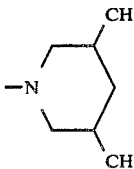 | 1.5251 |
| 293 | 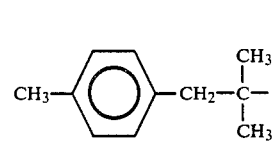 | CH₃ | 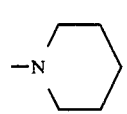 | 1.5150 |

-continued

| No. | Ar-O-R | R' | Amine | n |
|-----|--------|-----|-------|---|
| 294 | 4-CH₃-C₆H₄-O-CH₂-CH₂- | CH₃ | 3-methylpiperidin-1-yl | 1.5133 |
| 295 | 2-Cl-C₆H₄-O-CH₂-C(CH₃)₂- | CH₃ | pyrrolidin-1-yl | 1.5064 |
| 296 | 2-Cl-C₆H₄-O-CH₂-C(CH₃)₂- | CH₃ | piperidin-1-yl | 1.5082 |
| 297 | 2-Cl-C₆H₄-O-CH₂-C(CH₃)₂- | CH₃ | hexamethyleneimin-1-yl | 1.5090 |
| 298 | 2-Cl-C₆H₄-O-CH₂-C(CH₃)₂- | CH₃ | 2,6-dimethylpiperidin-1-yl | 1.5076 |
| 299 | 2-Cl-C₆H₄-O-CH₂-C(CH₃)₂- | CH₃ | 3,3-dimethylpiperidin-1-yl | 1.5045 |
| 300 | 2-Cl-C₆H₄-O-CH₂-C(CH₃)₂- | CH₃ | morpholin-4-yl | 1.5089 |
| 301 | 2-Cl-C₆H₄-O-CH₂-C(CH₃)₂- | CH₃ | 2,6-dimethylmorpholin-4-yl | 1.5062 |
| 302 | 2-Cl-C₆H₄-O-CH₂-C(CH₃)₂- | CH₃ | 4-methylpiperazin-1-yl | 1.5021 |
| 303 | 4-Cl-C₆H₄-O-CH₂-C(CH₃)₂- | CH₃ | -N(CH₃)(CH₂-C₆H₅) | 1.5171 |
| 304 | 4-Cl-C₆H₄-O-CH₂-C(CH₃)₂- | CH₃ | -N(c-C₆H₁₁)₂ | 1.5085 |

-continued
| | | | | |
|---|---|---|---|---|
| 305 | 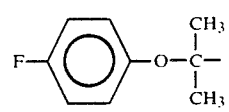 | CH₃ | 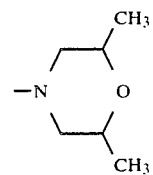 | |
| 306 | 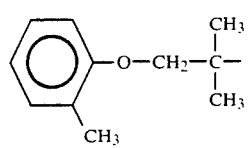 | CH₃ | 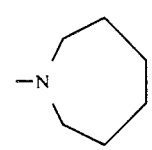 | 1.4995 |
| 307 | 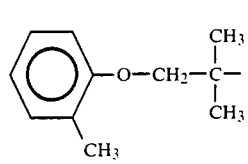 | CH₃ | 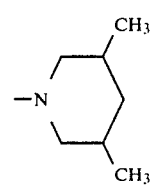 | 1.4909 |
| 308 | 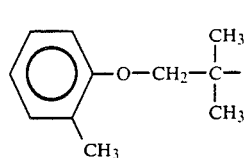 | CH₃ | 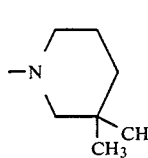 | 1.4908 |
| 309 | 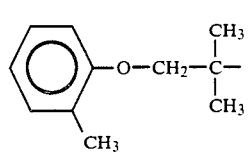 | CH₃ | 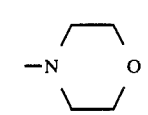 | 1.5002 |
| 310 | 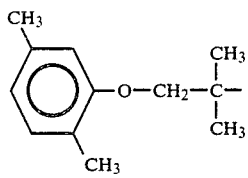 | CH₃ | 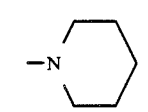 | 1.4980 |
| 311 | 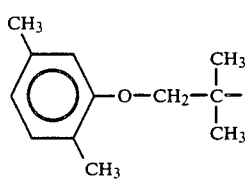 | CH₃ | 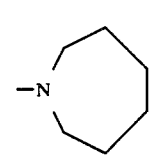 | 1.4941 |
| 312 | 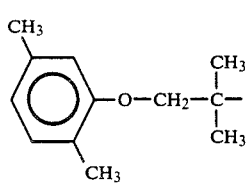 | CH₃ | 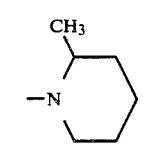 | 1.4953 |
| 313 | 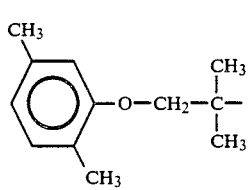 | CH₃ | 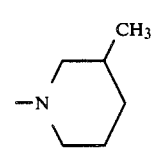 | 1.4939 |

-continued
| | | | |
|---|---|---|---|
| 314 | 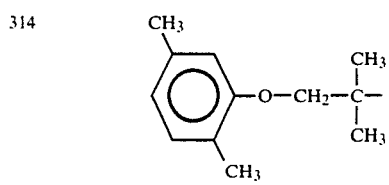 | CH₃ 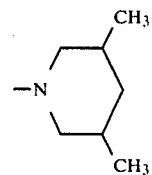 | 1.4902 |
| 315 | 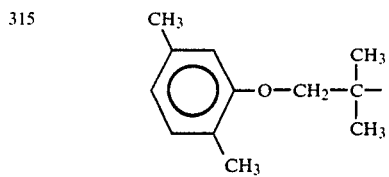 | CH₃ 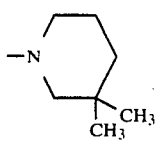 | 1.4900 |
| 316 | 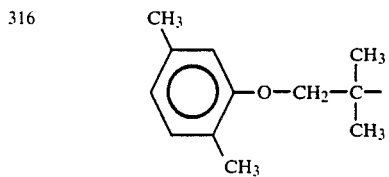 | CH₃ 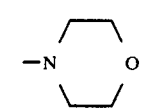 | 1.4979 |
| 317 | 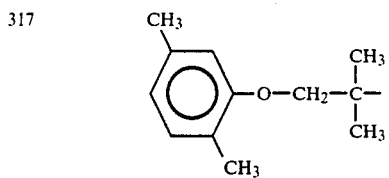 | CH₃ | 1.4905 |
| 318 | 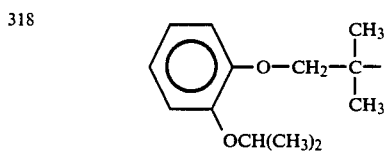 | CH₃ 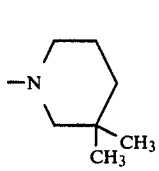 | 1.5041 |
| 319 | 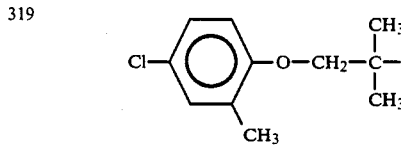 | CH₃ 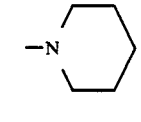 | 1.5058 |
| 320 | 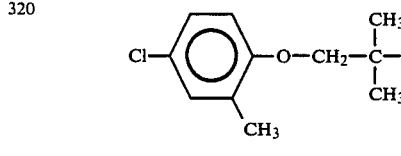 | CH₃ 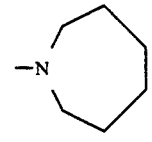 | 1.5068 |
| 321 | 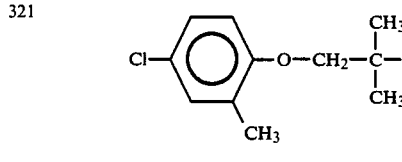 | CH₃ 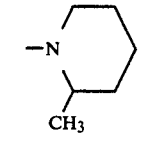 | 1.5031 |
| 322 | 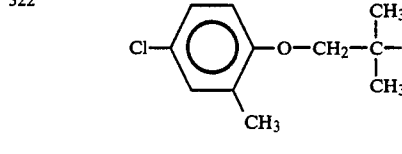 | CH₃ 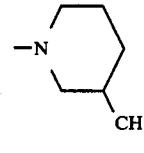 | 1.5021 |
| 323 | 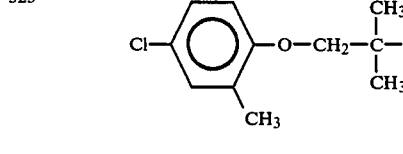 | CH₃ 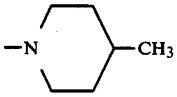 | 1.5012 |

| | | | | |
|---|---|---|---|---|
| 324 | 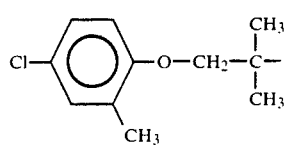 | CH₃ | 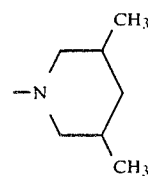 | 1.4984 |
| 325 | 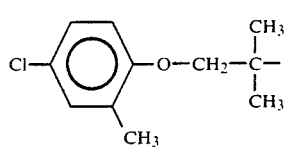 | CH₃ | 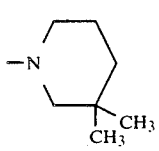 | 1.5069 |
| 326 | 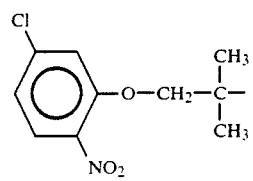 | CH₃ | 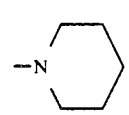 | oil |
| 327 | 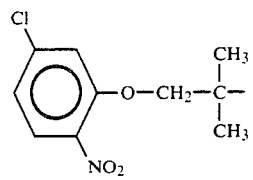 | CH₃ | 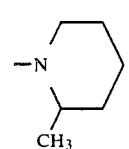 | oil |
| 328 | 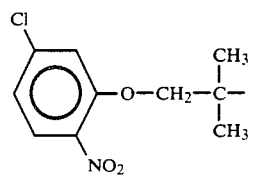 | CH₃ | 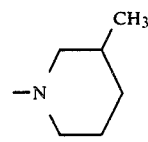 | oil |
| 329 | 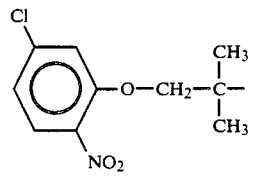 | CH₃ | 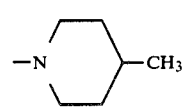 | oil |
| 330 | 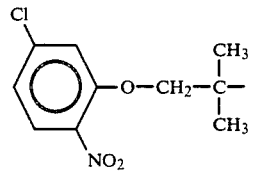 | CH₃ | 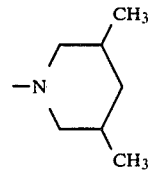 | oil |
| 331 | 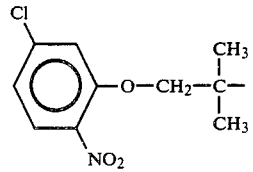 | CH₃ | 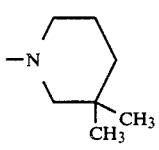 | oil |
| 322 | 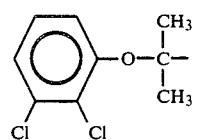 | CH₃ | 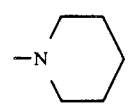 | |

-continued
| | | CH₃ | |
|---|---|---|---|
| 333 | 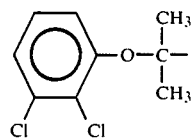 | CH₃ | 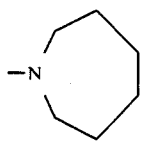 |
| 334 | 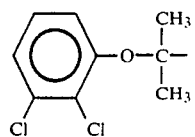 | CH₃ | 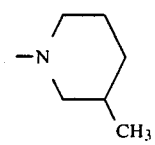 |
| 335 | 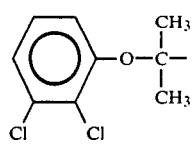 | CH₃ | 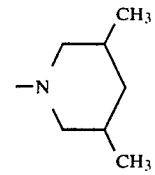 |
| 336 | 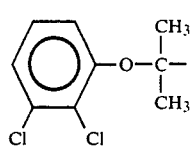 | CH₃ | 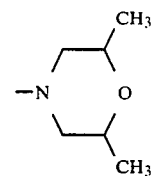 |
| 337 | 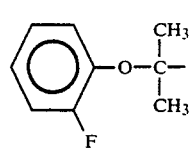 | CH₃ | 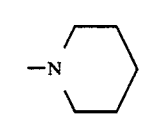 |
| 338 | 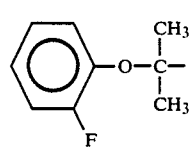 | CH₃ | 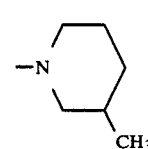 |
| 339 | 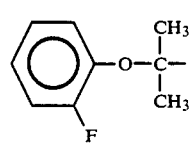 | CH₃ | 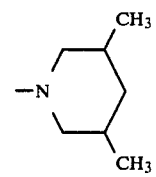 |
| 340 | 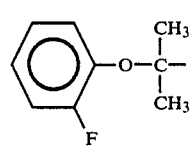 | CH₃ | 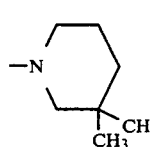 |
| 341 | 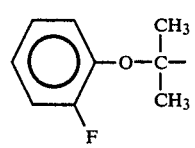 | CH₃ | 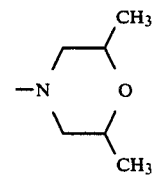 |
| 342 | 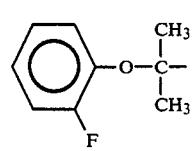 | CH₃ | 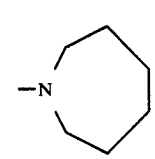 |

-continued
| | | | |
|---|---|---|---|
| 343 | 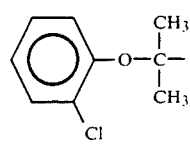 | CH₃ | 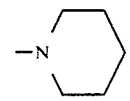 |
| 343 | 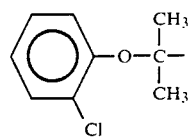 | CH₃ | 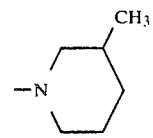 |
| 345 | 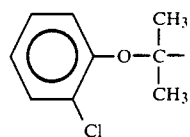 | CH₃ | 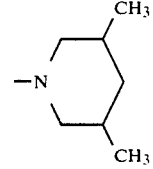 |
| 346 | 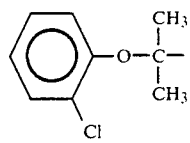 | CH₃ | 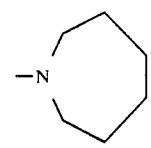 |
| 347 | 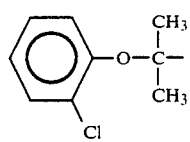 | CH₃ | 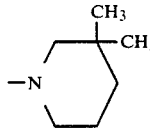 |
| 348 | 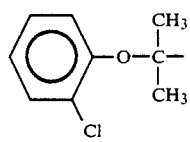 | CH₃ | 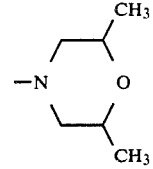 |
| 349 | 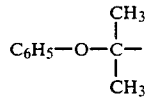 | CH₃ | 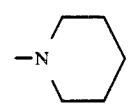 |
| 350 | 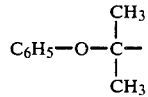 | CH₃ | 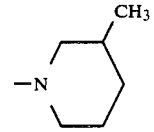 |
| 351 | 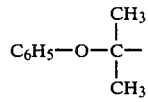 | CH₃ | 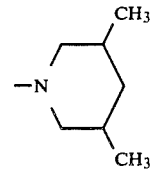 |
| 349 | 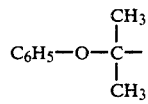 | CH₃ | 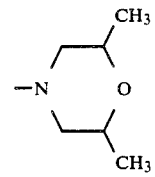 |

-continued
| | | | |
|---|---|---|---|
| 353 | 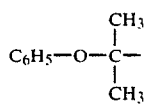 | CH₃ | 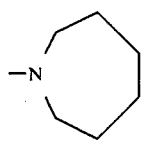 |
| 354 | 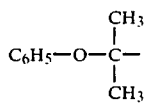 | CH₃ | 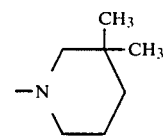 |
| 355 | 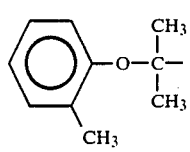 | CH₃ | 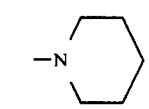 |
| 356 | 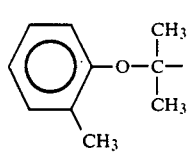 | CH₃ | 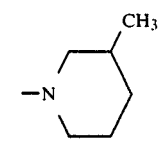 |
| 357 | 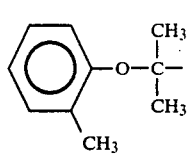 | CH₃ | 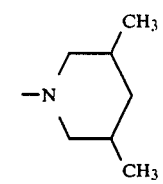 |
| 358 | 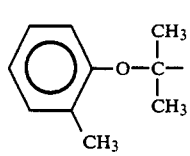 | CH₃ | 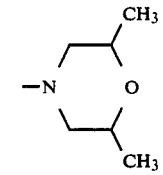 |
| 359 | 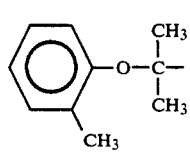 | CH₃ | 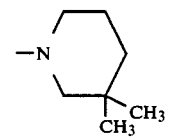 |
| 360 | 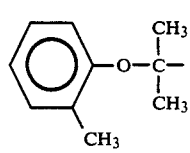 | CH₃ | 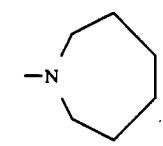 |
| 361 | 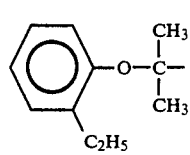 | CH₃ | 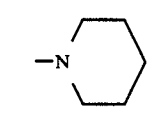 |
| 362 | 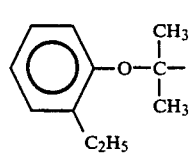 | CH₃ | 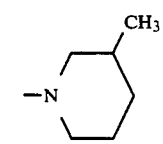 |

-continued
| | | | |
|---|---|---|---|
| 363 | 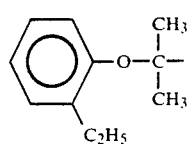 | CH₃ | 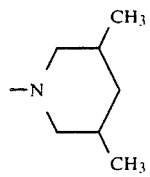 |
| 364 | 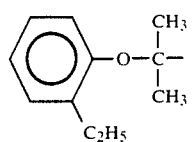 | CH₃ | 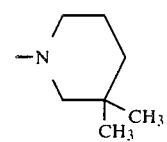 |
| 365 | 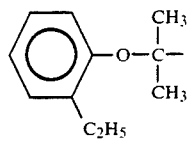 | CH₃ | 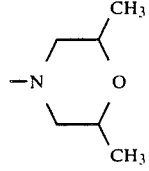 |
| 366 | 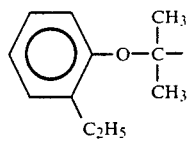 | CH₃ | 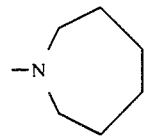 |
| 367 | 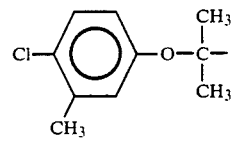 | CH₃ | 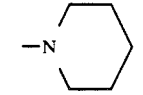 |
| 368 | 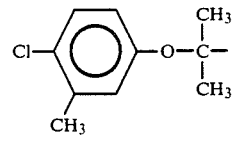 | CH₃ | 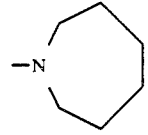 |
| 369 | 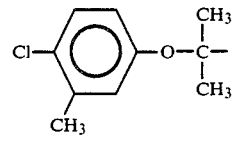 | CH₃ | 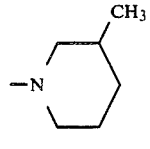 |
| 370 | 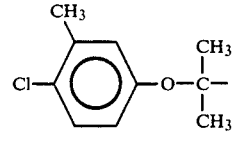 | CH₃ | 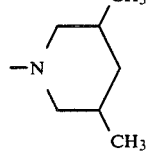 |
| 371 | 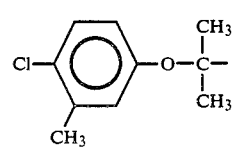 | CH₃ | 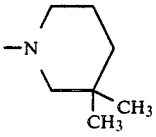 |
| 372 | 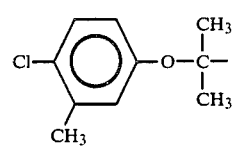 | CH₃ | 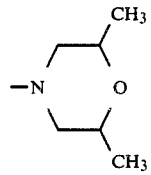 |

-continued
| | | | |
|---|---|---|---|
| 373 | 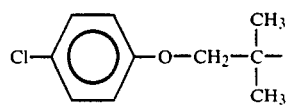 | CH₃ | 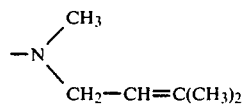 |
| 374 | 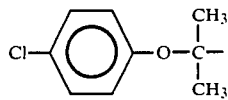 | CH₃ | 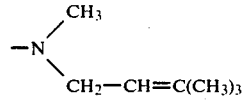 |
| 375 | 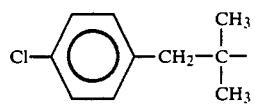 | CH₃ | 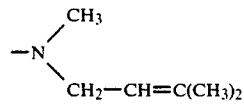 |
| 376 | 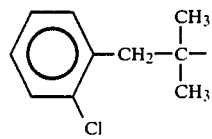 | CH₃ | 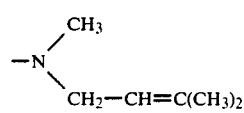 |
| 377 | 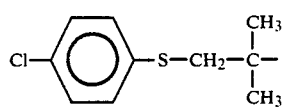 | CH₃ | 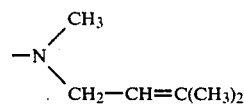 |
| 378 | 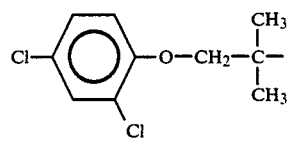 | CH₃ | 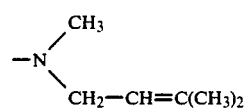 |
| 379 | 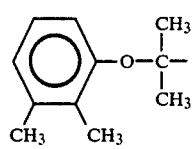 | CH₃ | 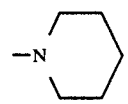 |
| 380 | 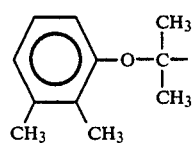 | CH₃ | 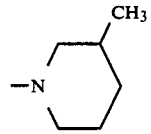 |
| 381 | 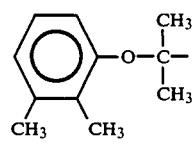 | CH₃ | 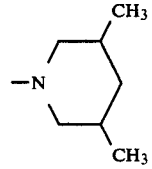 |
| 382 | 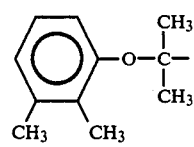 | CH₃ | 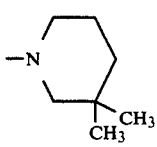 |
| 383 | 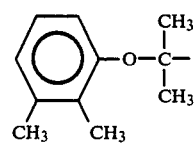 | CH₃ | 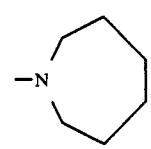 |

-continued
| | | |
|---|---|---|
| 384 | 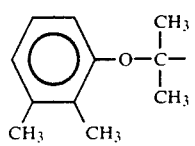 | 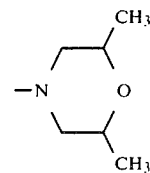 |
| 385 | 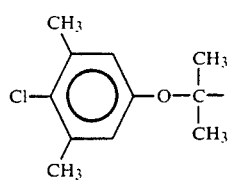 | CH₃ 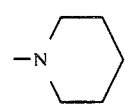 |
| 386 | 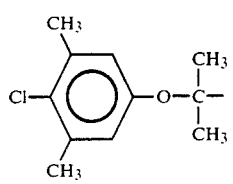 | CH₃ 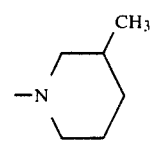 |
| 387 | 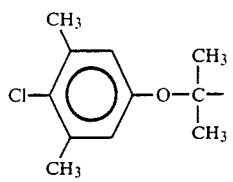 | CH₃ 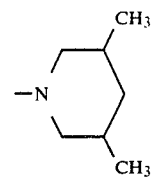 |
| 388 | 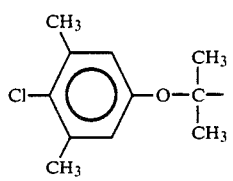 | CH₃ 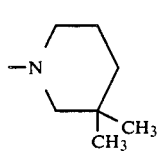 |
| 389 | 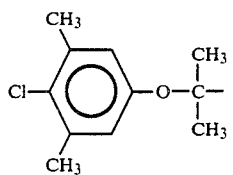 | CH₃ 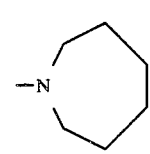 |
| 390 | 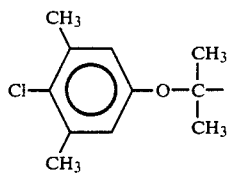 | CH₃ 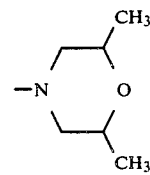 |
| 391 | 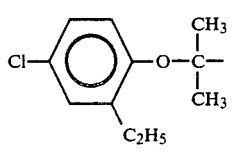 | CH₃ 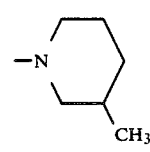 |
| 392 | 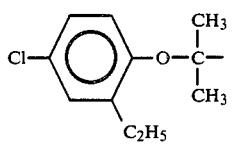 | CH₃ 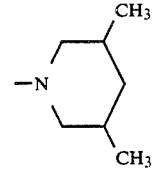 |

-continued
| | | |
|---|---|---|
| 393 | 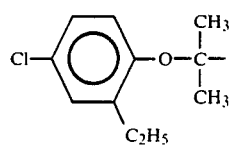 | CH3 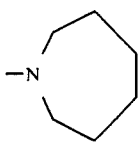 |
| 394 | 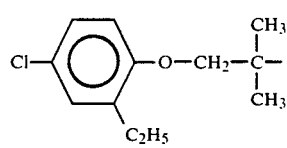 | CH3 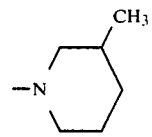 |
| 395 | 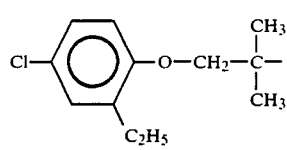 | CH3 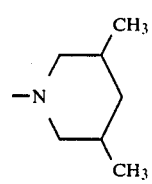 |
| 396 | 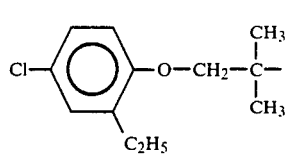 | CH3 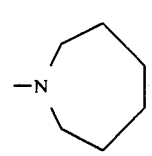 |
| 397 | 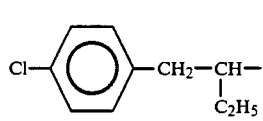 | CH3 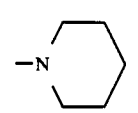 |
| 398 | 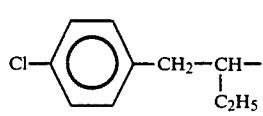 | CH3 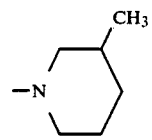 |
| 399 | 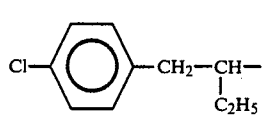 | CH3 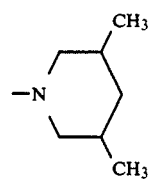 |
| 400 | 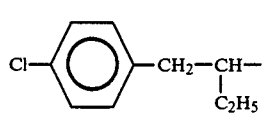 | CH3 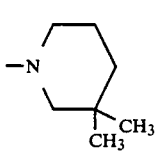 |
| 401 | 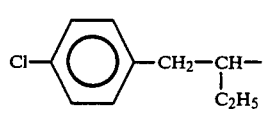 | CH3 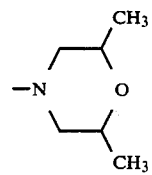 |
| 402 | 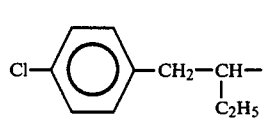 | CH3 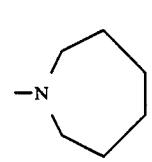 |

| | | -continued | |
|---|---|---|---|
| 403 | 4-Cl-C6H4-CH=C(C2H5)- | CH3 | piperidin-1-yl |
| 404 | 4-Cl-C6H4-CH=C(C2H5)- | CH3 | azepan-1-yl (hexamethyleneimino) |
| 405 | 4-Cl-C6H4-CH=C(C2H5)- | CH3 | 3-methylpiperidin-1-yl |
| 406 | 4-Cl-C6H4-CH=C(C2H5)- | CH3 | 3,5-dimethylpiperidin-1-yl |
| 407 | 4-Cl-C6H4-CH=C(C2H5)- | CH3 | 3,3-dimethylpiperidin-1-yl |
| 408 | 4-Cl-C6H4-CH=C(C2H5)- | CH3 | 2,6-dimethylmorpholin-4-yl |
| 409 | C6H11-CH2-C(CH3)2- | CH3 | piperidin-1-yl |
| 410 | C6H11-CH2-C(CH3)2- | CH3 | azepan-1-yl |
| 411 | C6H11-CH2-C(CH3)2- | CH3 | 3-methylpiperidin-1-yl |
| 412 | C6H11-CH2-C(CH3)2- | CH3 | 3,5-dimethylpiperidin-1-yl |

| | | -continued | | |
|---|---|---|---|---|
| 413 | 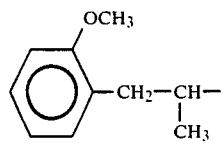 | CH₃ | 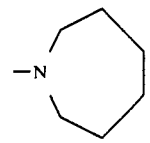 | |
| 414 | 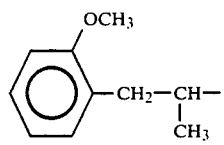 | CH₃ | 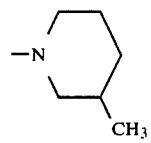 | |
| 415 | 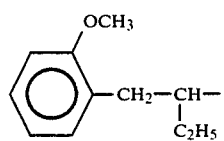 | CH₃ | 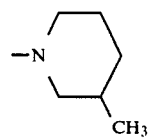 | |
| 416 | 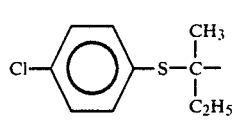 | CH₃ | 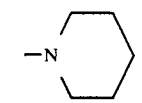 | |
| 417 | 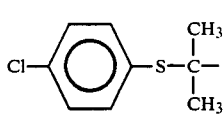 | CH₃ | 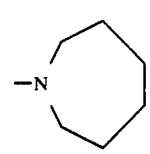 | |
| 418 | 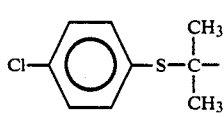 | CH₃ | 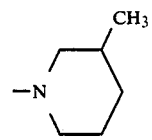 | |
| 419 | 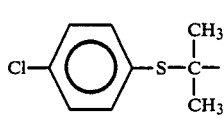 | CH₃ | 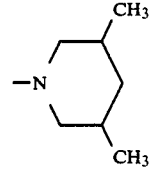 | |
| 420 | 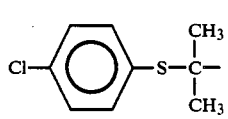 | CH₃ | 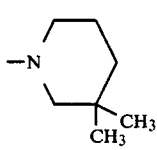 | |
| 421 | 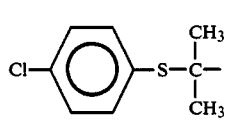 | CH₃ | 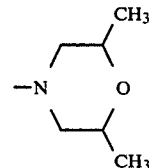 | |
| 422 | 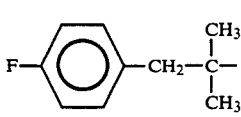 | CH₃ | 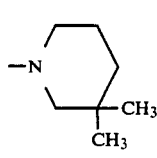 | 1.4986 |

423 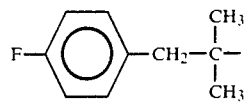  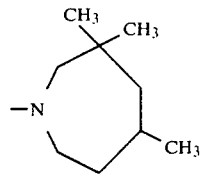 1.5002

Use examples

In the fungicidal use examples which follow, the compounds indicated below are employed as comparative substances.

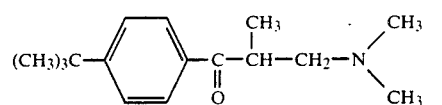 (A)

the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet 100% relative atmospheric humidity and at about 20° C.

Evaluation is carried out 3 days after the inoculation.

In this test, a clearly superior activity compared with the prior art is shown, for example, by the compounds according to the following preparation examples: 71 and 78.

(B)

TABLE A

| | Phytophthora test (tomato)/protective | |
|---|---|---|
| Active compound | | Infestation in % of an active compound concentration of 0.005% |
| (CH₃)₃C—⟨⟩—C(=O)—CH(CH₃)—CH₂—N(CH₃)₂ (A) (known) | | 60 |
| Cl—⟨⟩—O—CH₂—C(CH₃)₂—[C(CH₃)(O—O)]—CH₂—N(piperidine) × HCl (71) | | 16 |
| Cl—⟨⟩—O—CH₂—C(CH₃)₂—[C(CH₃)(O—O)]—CH₂—N(triazole) (78) | | 21 |

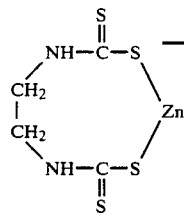

EXAMPLE A

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and

EXAMPLE B

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator 10 days. Germination of the barley, and possibly also of the fungus spores, is thereby initiated. 2 batches of 50 grains of the pregerminated barley are subsequently sown 3 cm deep in standard soil according to the following preparation examples: 71, 74, 77, 98 and 104.

TABLE B

Drechslera graminea test (barley)/seed treatment
(syn. *Helminthosporium gramineum*)

| Active compound | Amount of active compound used in mg/kg of seed | Diseased plants as % of the total plants emerged |
|---|---|---|
| untreated | | 24.0 |
| 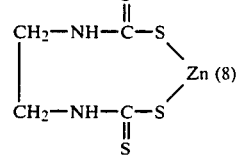 (known) | 600 | 19.0 |
| 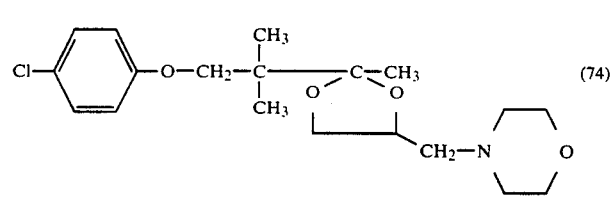 (74) | 500 | 1.1 |
| 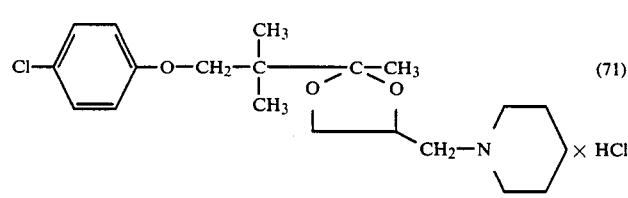 (71) | 500 | 1.2 |
| 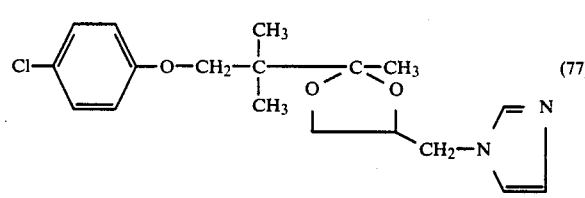 (77) | 500 | 3.5 |
| 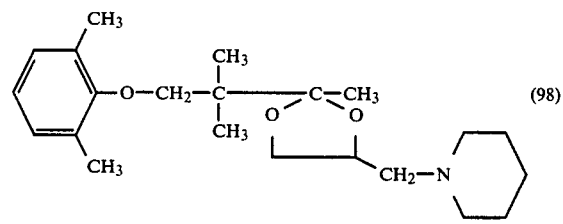 (98) | 500 | 2.5 |
| 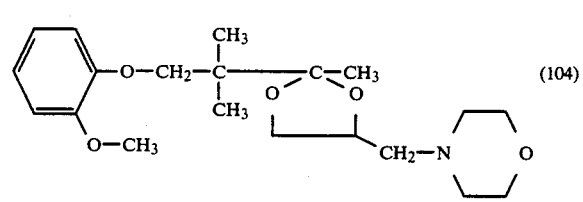 (104) | 500 | 3.6 | and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds

EXAMPLE C

Erysiphe test (barley)/protective

Solvent: 100 parts by weight of dimethylformamide

Emulsifier: 0.25 parts by weight of alkylaryl polygylcol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminisi f. sp. hordei.* the plants are placed in a greenhouse at a temperature of about 25° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 29, 71, 72, 73, 74, 75, 76, 78, 89, 90, 92, 94, 95, 97, 98, 100, 102, 104, 105, 106, 107, 113.

TABLE C

Erysiphe test (barley)/protective

| Active compound | Active compound concentration in the spray Liquor in % by weight | Disease infestation as % of the untreated control |
|---|---|---|
| 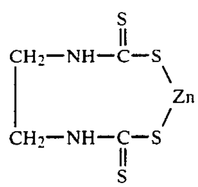  (B) (known) | 0.025 | 100 |
| 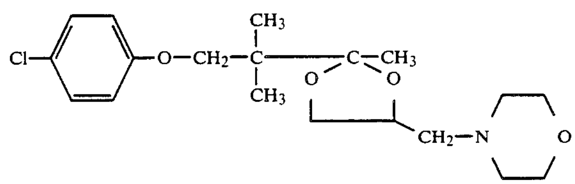  (74) | 0.025 | 3.8 |
| 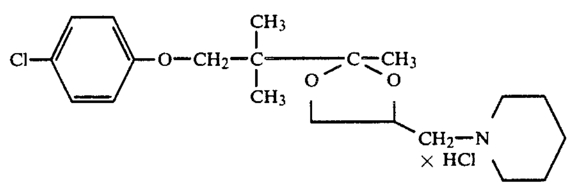  (71) | 0.025 | 3.8 |
| 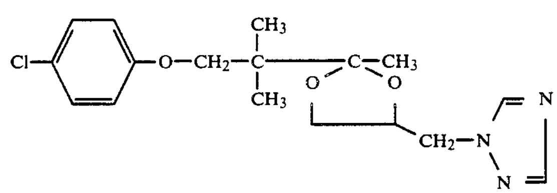  (78) | 0.025 | 25.0 |
| 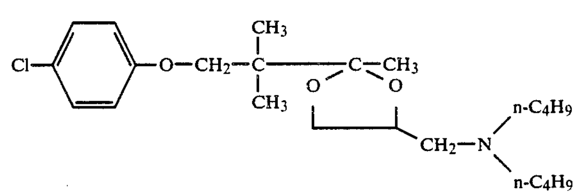  (76) | 0.025 | 12.5 |

TABLE C-continued

Erysiphe test (barley)/protective

| Active compound | Active compound concentration in the spray Liquor in % by weight | Disease infestation as % of the untreated control |
|---|---|---|
| (73) 4-Cl-C₆H₄-O-CH₂-C(CH₃)₂-C(CH₃)(O-O)-CH₂-N(piperidine-4-phenyl) | 0.025 | 12.5 |
| (29) 2,5-diCl-C₆H₃-C(CH₃)(O-O)-CH(CH₂-piperidine) | 0.025 | 25.0 |
| (72) 4-Cl-C₆H₄-O-CH₂-C(CH₃)₂-C(CH₃)(O-O)-CH(CH₂-N(2-methylpiperidine)) | 0.025 | 12.5 |
| (90) 2-CH₃-C₆H₄-O-CH₂-C(CH₃)₂-C(CH₃)(O-O)-CH(CH₂-N(2,6-dimethylmorpholine)) | 0.025 | 12.5 |
| (89) 2-CH₃-C₆H₄-O-CH₂-C(CH₃)₂-C(CH₃)(O-O)-CH(CH₂-N(piperidine)) | 0.025 | 0.0 |

TABLE C-continued

Erysiphe test (barley)/protective

| Active compound | Active compound concentration in the spray Liquor in % by weight | Disease infestation as % of the untreated control |
|---|---|---|
| (113) Cyclohexyl-C₆H₄-O-CH₂-C(CH₃)₂-[dioxolane with C-CH₃, CH₂-N(piperidine)] | 0.025 | 25.0 |
| (92) CH₃-C₆H₄-O-CH₂-C(CH₃)₂-[dioxolane with C-CH₃, CH₂-N(CH₂)₃CH₃ / (CH₂)₃CH₃] | 0.025 | 12.5 |
| (105) 2-C₂H₅-C₆H₄-O-CH₂-C(CH₃)₂-[dioxolane with C-CH₃, CH₂-N(piperidine)] | 0.025 | 8.8 |
| (106) 2-C₂H₅-C₆H₄-O-CH₂-C(CH₃)₂-[dioxolane with C-CH₃, CH₂-N(morpholine)] | 0.025 | 12.5 |
| (107) 2-C₂H₅-C₆H₄-O-CH₂-C(CH₃)₂-[dioxolane with C-CH₃, CH₂-N(N-methylpiperazine)] | 0.025 | 16.3 |

TABLE C-continued
| Active compound | Active compound concentration in the spray Liquor in % by weight | Disease infestation as % of the untreated control |
|---|---|---|
| (95) 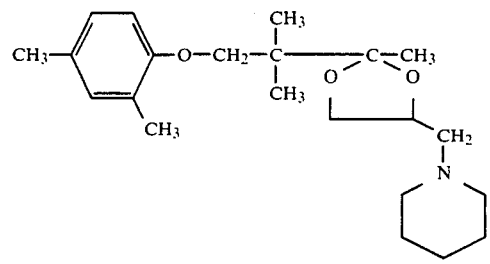 | 0.025 | 10.0 |
| (98) 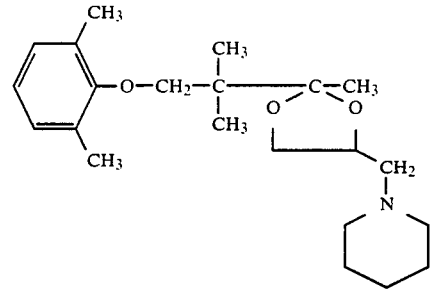 | 0.025 | 3.8 |
| (97) 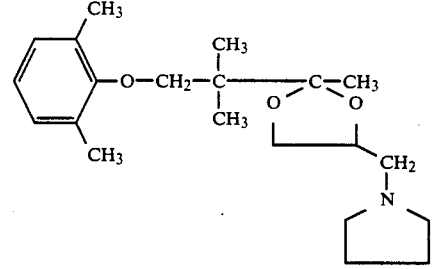 | 0.025 | 12.5 |
| (94) 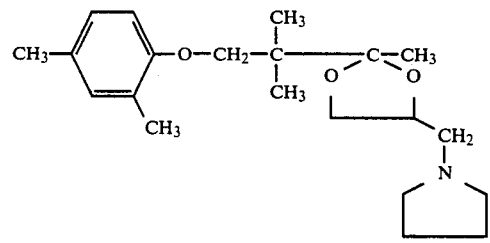 | 0.025 | 12.5 |
| (100) 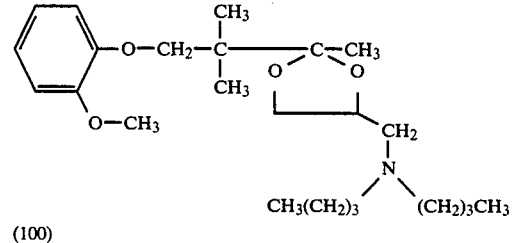 | 0.025 | 33.8 |

TABLE C-continued

Erysiphe test (barley)/protective

| Active compound | Active compound concentration in the spray Liquor in % by weight | Disease infestation as % of the untreated control |
|---|---|---|
| (104) ![structure] | 0.025 | 21.3 |
| (102) ![structure] | 0.025 | 12.5 |
| (75) ![structure] | 0.025 | 33.8 |

We claim:

1. A method of combating fungi which comprises applying to such fungi or to a fungus habitat a fungicidally effective amount of a substituted aminoketal of the formula

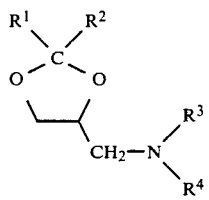

in which
$R^1$ represents straight-chain or branched alkyl having 1 to 18 carbon atoms; straight-chain or branched halogenoalkyl having 1 to 12 carbon atoms and 1 to 5 halogen atoms, straight-chain or branched cyanoalkyl having 1 to 4 carbon atoms in the alkyl part, aralkyl, aryloxyalkyl, aralkyloxyalkyl, arylthioalkyl, arylsulphinylalkyl and arylsulphonylalkyl, each having 1 to 6 carbon atoms in each alkyl part and 6 to 10 carbon atoms in the aryl part, the radicals in each case being optionally monosubstituted or polysubstituted by at least one radical independently selected from the group consisting of halogen, cyano, nitro, alkyl, alkoxy and alkylthio each having 1 to 4 carbon atoms, halogenoalkyl, halogenoalkoxy, halogenoalkylthio, each having 1 or 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, or by alkyl having 1 to 4 carbon atoms; and represents cycloalkylalkyl having 1 to 4 carbon atoms in the alkyl part and 3 to 7 carbon atoms in the cycloalkyl part which is optionally monosubstituted or polysubstituted by alkyl having 1 to 4 carbon atoms, and also represents straight-chain or branched alkenyl or alkinyl, each having 2 to 6 carbon atoms, cycloalkyl which has 3 to 7 carbon atoms and is optionally monosubstituted or polysubstituted by identical or different alkyl radicals having 1 to 4 carbon atoms, or represents aryl having 6 to 10 carbon atoms and arylalkenyl having 2 to 6 carbon atoms in the alkenyl part and 6 to 10 carbon atoms in the aryl part, each of which is optionally monosubstituted or polysubstituted on the aryl by at least one radical independently selected from the group consisting of halogen, cyano, nitro; alkyl, alkoxy, alkylthio, each having 1 to 4 carbon atoms; halogenoalkyl, halogenoalkoxy, halogenoalkylthio, each having 1 or 2 carbon atoms and 1 to 5 halogen atoms, cycloalkyl having 5 to 7 carbon atoms, alkoxycarbonyl having 1 to 4 carbon atoms in the alkyl part, and phenoxy or phenyl which is optionally substituted by halogen, or by alkyl having 1 to 4 carbon atoms;

$R^2$ has the meaning of $R^1$ and may be identical or different to this radical, and additionally represents hydrogen, $R^3$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloalkyl which has 5 to 7 carbon atoms and is optionally monosubstituted or polysubstituted by identical or different alkyl groups having 1 to 4 carbon atoms, and aryl having 6 to 10 carbon atoms or aralkyl having 1 or 2 carbon atoms in the alkyl part and 6 to 10 carbon atoms in the aryl part, each of which radicals is optionally monosubstituted or polysubstituted on the aryl by at least one radical independently selected from the group consisting of halogen, alkyl having 1 to 4 carbon atoms and halogenoalkyl having 1 or 2 carbon atoms and 1 to 5 halogen atoms; and $R^4$ represents straight-chain or branched alkyl having 1 to 12 carbon atoms, straight-chain or branched alkenyl having 3 to 12 carbon atoms, straight-chain or branched alkinyl having 3 to 7 carbon atoms, cycloakyl which has 5 to 7 carbon atoms and is optionally monosubstituted or polysubstituted by identical or different alkyl groups having 1 to 4 carbon atoms, and aryl having 6 to 10 carbon atoms in the alkyl part and 6 to 10 carbon atoms in the aryl part, each of which radicals is optionally monosubstituted or polysubstituted on the aryl by at least one radical independently selected from the group consisting of halogen, alkyl having 1 to 4 carbon atoms and halogenoalkyl having 1 or 2 carbon atoms and 1 to 5 halogen atoms or a physiologically tolerated addition product thereof with an acid or metal salt.

2. A process according to claim 1, in which $R^1$ represents straight-chain or branched alkyl having 1 to 12 carbon atoms, cyclopropyl, cyclopentyl, cyclohexyl, straight-chain or branched halogenoalkyl having 1 to 6 carbon atoms and 1 to 5 halogen atoms, or phenyl, phenylalkyl, phenoxyalkyl, benzyloxyalkyl, phenylthioalkyl, phenylsulphinylalkyl and phenylsulphonylalkyl, each having 1 to 5 carbon atoms in the alkyl part, the radicals in each case being optionally monosubstituted, disubstituted or trisubstituted by identical or different substituents, and phenylalkenyl which has 2 to 4 carbon atoms in the alkenyl part and is optionally monosubstituted, disubstituted of trisubstituted on the phenyl by at least one radical independently selected from the group consisting of fluorine, chlorine, bromine, cyano, nitro, methyl, methoxy, methylthio, ethyl, ethoxy, ethylthio, n- and i-propyl, isopropoxy, n-, iso-, sec.- and t-butyl, trifluoromethyl, trifluoromethoxy, trifluoromethylthio, cyclohexyl, methoxycarbonyl, ethoxycarbonyl and phenoxy or phenyl which is optionally substituted by fluorine, chlorine or methyl;

$R^2$ represents straight-chain or branched alkyl having 1 to 10 carbon atoms, benzyl and phenyl which is optionally monosubstituted, disubstituted or trisubstituted on the phenyl by at least one radical independently selected from the group consisting of fluorine, chlorine, bromine, cyano, nitro, trifluoromethyl, trifluoromethoxy, trufluoromethylthio, methoxycarbonyl and ethoxycarbonyl, or represents cyclopropyl, cyclopentyl and cyclohexyl, $R^3$ represents methyl, ethyl, n- and i-propyl, n-, i-, sec.- and t-butyl, n-pentyl, n-hexyl, n-heptyl, n-octyl, n-nonyl, n-decyl, n-dodecyl, allyl, propargyl, 2-butenyl, cyclopentyl or cyclohexyl, and phenyl or benzyl, each of which is optionally monosubstituted or disubstituted by identical or different substituents from the group consisting of fluorine, chlorine, methyl and trifluoromethyl, and $R^4$ represents n- and i-propyl, n-, i-, sec.- and t-butyl, n-pentyl, n-hexyl, a-heptyl, n-octyl, n-nonyl, n-decyl, allyl, propargyl, but-2-enyl, cyclopentyl or cyclohexyl, and phenyl or benzyl, each of which is optionally monosubstituted or disubstituted by identical or different substituents from the group consisting of fluorine, chlorine, methyl and trifluoromethyl.

3. A process according to claim 1, in which $R^1$ represents straight-chain or branched alkyl having 1 to 5 carbon atoms, and phenylakenyl, phenylalkyl, phenoxyalky, benzyloxyalky, phenylthioalky, phenylsulphinylalkyl and phenylsulphonylalkyl, each of which has up to 5 carbon atoms in the alkyl part of alkenyl part and is optionally monosubstituted, disubstituted or trisubstituted on the phenyl by at least one radical independently selected from the group consisting of fluorine, chlorine, bromine, methyl, ethyl, n- and i-propyl, t-butyl-, methoxy, ethoxy, isopropoxy, cyclohexyl, trifluoromethyl), trifluoromethoxy, trifluoromethylthio, methoxycarbonyl, ethoxycarbonyl, nitro, cyano, phenyl and phenoxy $R^2$ represents straight-chain or branched alkyl having 1 to 4 carbon atoms or hydrogen;

$R^3$ represents methyl, ethyl, n- and i-propyl or n-, i- and t-butyl; and $R^4$ represents methyl, ethyl, n- and i-propyl, n- and i-butyl, pentyl or hexyl.

4. A process according to claim 1, in which $R^1$ represents the groupings

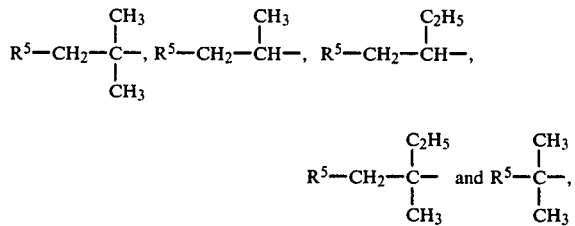

$R^5$ represents phenyl, phenoxy, phenylthio, phenysulphinyl or phenylsulphonyl, each of which is optionally monosubstituted to trisubstituted by at least one radical independently selected from the group consisting of fluorine, chlorine, bromine, nitro, cyclohexyl, straight-chain or branched alkyl having 1 to 4 carbon atoms, straight-chained or branched alkoxy having 1 to 3 carbon atoms and alkoxycarbonyl having 1 or 2 carbon atoms in the alkoxy part, $R^2$ represents a straight-chain or branched alkyl having 1 to 4 carbon atoms, $R^3$ represents a straight-chain or branched alkyl having 1 to 4 carbon atoms or straight-chain or branched alkenyl having 3 to 5 carbon atoms, and $R^4$ represents straight-chain or branched alkyl having 1 to 4 carbon atoms.

5. A process according to claim 1, in which $R^1$ represents the groupings $$R^6-CH=\overset{CH_3}{\underset{|}{C}} \quad \text{and} \quad R^6-CH=\overset{C_2H_5}{\underset{|}{C}},$$

wherein $R^6$ represents phenyl which is in each case optionally monosubstituted to trisubstituted by at least one radical independently selected from the group consisting of fluorine, chlorine, bromine, nitro, cyclohexyl, straight-chain or branched alkyl or alkoxy, each having 1 or 2 carbon atoms in the alkyl part, and $R^2$ represents straight-chain or branched alkyl having 1 to 4 carbon atoms, $R^3$ represents straight-chain or branched alkyl having 1 to 4 carbon atoms or straight-chain or branched alkenyl having 3 to 5 carbon atoms, and $R^4$ represents straight-chain or branched alkyl having 1 to 4 carbon atoms.

6. A substituted aminolketal of the formula $$\begin{array}{c} R^{1'} \quad R^{2'} \\ \diagdown \diagup \\ C \\ O \diagup \quad \diagdown O \\ \diagdown \diagup \\ CH_2-N \diagup^{R^{3'}}_{R^{4'}} \end{array}$$

in which $R^{1'}$ represents the groupings $$R^5-CH_2-\overset{CH_3}{\underset{\underset{CH_3}{|}}{C}}-, \quad R^5-CH_2-\overset{CH_3}{\underset{|}{CH}}-, \quad R^5-CH_2-\overset{C_2H_5}{\underset{|}{CH}},$$

$$R^5-CH_2-\overset{C_2H_5}{\underset{\underset{CH_3}{|}}{C}}-, \quad R^5-\overset{CH_3}{\underset{\underset{CH_3}{|}}{C}}- \quad \text{and} \quad R^5-CH_2-,$$

wherein $R^5$ represents phenoxy, phenylthio, phenylsulphinyl or phenylsulphonyl, each of which is optionally monosubstituted to trisubstituted by at least one radical independently selected from the group consisting of fluorine, chlorine, bromine, nitro, cyclohexyl, straight-chain or branched alkyl having 1 to 4 carbon atoms, straight-chain or branched alkoxy having 1 to 3 carbon atoms and alkoxycarbonyl having 1 or 2 carbon atoms in the alkoxy part, $R^{2'}$ represents hydrogen, straight-chain or branched alkyl having 1 to 10 carbon atoms; and benzyl or phenyl which is optionally monosubstituted to trisubstituted on the phenyl by at least one radical independently selected from the group consisting of fluorine, chlorine, bromine, cyano, nitro, trifluoromethyl, trifluoromethoxy, trifluoromethylthio, methoxycarbonyl and ethoxycarbonyl, $R^{3'}$ represents methyl, ethyl, n- and i-propyl, n-, i-, sec.- and t-butyl, n-pentyl, n-hexyl, n-heptyl, n-octyl, n-nonyl, n-decyl, n-dodecyl, allyl, propargyl, but-2-enyl, cyclopentyl and cyclohexyl, and benzyl or phenyl, each of which is optionally monosubstituted or disubstituted by identical or different substituents selected from the group consisting of fluorine, chlorine, methyl and trifluoromethyl and $R^{4'}$ represents n- and i-propyl, n-, i-, sec.- and t-buthyl, n-pentyl, n-hexyl, n-heptyl, n-octyl, n-nonyl, n-decyl, allyl, propargyl, but-2-enyl, cyclopentyl and cyclohexyl, and phenyl or benzyl, each of which is optionally monosubstituted or disubstituted by identical or different substituents selected from the group consisting of fluorine, chlorine, methyl and trifluoromethyl.

7. A substituted aminoketal of the formula $$\begin{array}{c} R^{1'} \quad R^{2'} \\ \diagdown \diagup \\ C \\ O \diagup \quad \diagdown O \\ \diagdown \diagup \\ CH_2-N \diagup^{R^{3'}}_{R^{4'}} \end{array}$$

in which $R^{1'}$ represents the groupings $$R^6-CH=\overset{CH_3}{\underset{|}{C}}- \quad \text{and} \quad R^6-CH=\overset{C_2H_5}{\underset{|}{C}}-,$$

wherein $R^6$ represents phenyl which in each case is optionally monosubstituted to trisubstituted by at least one radical independently selected from the group consisting of fluorine, chlorine, bromine, nitro, cyclohexyl, straight-chain or branched alkyl or alkoxycarbonyl having 1 or 2 carbon atoms in the $R^{2'}$ represents straight-chain or branched alkyl having 1 to 4 carbon atoms, $R^{3'}$ represents straight-chain or branched alkyl having 1 to 4 carbon atoms or straight-chain or branched alkenyl having 3 to 5 carbon atoms, and $R^{4'}$ represents straight-chain or branched alkyl having 1 to 4 carbon atoms.

8. A compound according to claim 6 wherein such compound is 2-(4-chlorophenoxy-t-butyl)-4-(di-n-butylaminomethyl)-2-methyl-1,3-dioxolane of the formula $$Cl-\underset{}{\underset{}{\bigcirc}}-O-CH_2-\overset{CH_3}{\underset{\underset{CH_3}{|}}{C}}\diagdown \begin{array}{c} \\ O \diagup \overset{CH_3}{\underset{|}{C}} \diagdown O \\ \diagdown \diagup \\ CH_2-N \diagup^{C_4H_9-n}_{C_4H_9-n} \end{array}$$

or a physiologically tolerated addition product thereof with an acid or metal salt.

9. A compound according to claim 6 wherein such compound is 4-(di-n-butylaminomethyl)-2-methyl-2-(4-methylphenoxy-t-butyl)-1,3-dioxolane of the formula

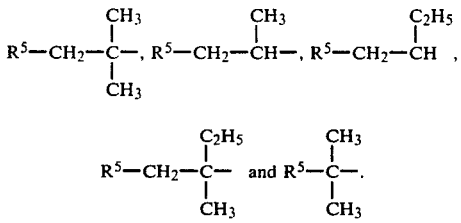

or a physiologically tolerated addition product thereof with an acid or metal salt.

10. A compound according to claim 6 wherein such compound is (4-(di-n-butylaminomethyl)-2-(2-methoxyphenoxy-t-butyl)-2-methyl-1,3-dioxolane of the formula

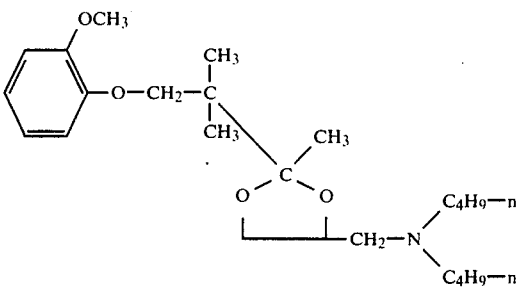

or a physiologically tolerated addition product thereof with an acid or metal salt.

11. A fungicidal composition comprising a fungicidally effective amount of a compound or addition product thereof according to claim 6 in admixture with a diluent.

12. A fungicidal composition comprising a fungicidally effective amount of a compound or addition product thereof according to claim 7 in admixture with a diluent.

13. A compound according to claim 6, in which $R^{1'}$ represents the groupings $$R^5-CH_2-\underset{CH_3}{\overset{CH_3}{\underset{|}{\overset{|}{C}}}}-, \quad R^5-CH_2-\overset{CH_3}{\underset{|}{CH}}-, \quad R^5-CH_2-\overset{C_2H_5}{\underset{|}{CH}},$$

$$R^5-CH_2-\underset{CH_3}{\overset{C_2H_5}{\underset{|}{\overset{|}{C}}}}- \quad \text{and} \quad R^5-\underset{CH_3}{\overset{CH_3}{\underset{|}{\overset{|}{C}}}}-.$$

* * * * *